United States Patent
Skaria et al.

(10) Patent No.: US 11,116,701 B2
(45) Date of Patent: Sep. 14, 2021

(54) STABILIZED CALCIUM PHOSPHATE

(71) Applicant: MODERN IDEAS LLC, Watertown, MA (US)

(72) Inventors: Sunny Skaria, Concord, MA (US); Kenneth Berk, Newton, MA (US)

(73) Assignee: Modern Ideas LLC, Watertown, MA (US)

( * ) Notice: Subject to any disclaimer, the term of this patent is extended or adjusted under 35 U.S.C. 154(b) by 0 days.

(21) Appl. No.: 16/245,983

(22) Filed: Jan. 11, 2019

(65) Prior Publication Data

US 2019/0142703 A1 May 16, 2019

Related U.S. Application Data

(62) Division of application No. 14/638,289, filed on Mar. 4, 2015, now Pat. No. 10,219,986.

(51) Int. Cl.

| | |
|---|---|
| A61K 6/838 | (2020.01) |
| C01B 25/32 | (2006.01) |
| C09J 4/00 | (2006.01) |
| A61K 6/20 | (2020.01) |
| A61K 6/62 | (2020.01) |
| A61K 6/69 | (2020.01) |
| A61K 6/71 | (2020.01) |
| A61K 6/74 | (2020.01) |
| A61K 6/77 | (2020.01) |
| A61K 6/887 | (2020.01) |
| B05D 5/06 | (2006.01) |
| C08F 222/10 | (2006.01) |

(52) U.S. Cl.
CPC ............... *A61K 6/838* (2020.01); *A61K 6/20* (2020.01); *A61K 6/62* (2020.01); *A61K 6/69* (2020.01); *A61K 6/71* (2020.01); *A61K 6/74* (2020.01); *A61K 6/77* (2020.01); *A61K 6/887* (2020.01); *B05D 5/061* (2013.01); *C01B 25/32* (2013.01); *C09J 4/00* (2013.01); *C08F 222/1065* (2020.02)

(58) Field of Classification Search
CPC .......... A61K 6/838; A61K 6/887; A61K 6/77; A61K 6/74; A61K 6/71; A61K 6/69; A61K 6/62; A61K 6/20; B05D 5/061; C09J 4/00; C01B 25/32; C08F 222/1065
See application file for complete search history.

(56) References Cited

U.S. PATENT DOCUMENTS

| | | | |
|---|---|---|---|
| 4,806,381 A | 2/1989 | Engelbrecht et al. | |
| 4,849,193 A | 7/1989 | Palmer et al. | |
| 4,872,936 A | 10/1989 | Engelbrecht | |
| RE33,161 E | 2/1990 | Brown et al. | |
| RE33,221 E | 5/1990 | Brown et al. | |
| 5,037,639 A | 8/1991 | Tung | |
| 5,238,491 A | 8/1993 | Sugihara et al. | |
| 5,460,803 A | 10/1995 | Tung | |
| 5,508,342 A | 4/1996 | Antonucci et al. | |
| 5,522,893 A | 6/1996 | Chow et al. | |
| 5,650,176 A | 7/1997 | Lee et al. | |
| 5,676,976 A | 10/1997 | Lee et al. | |
| 6,024,985 A | 2/2000 | Simkiss et al. | |
| 6,056,930 A | 5/2000 | Tung | |
| 6,114,408 A | 9/2000 | Dickens | |
| 6,214,368 B1 | 4/2001 | Lee et al. | |
| 6,254,872 B1 | 6/2001 | Frey et al. | |
| 63,525,992 | 12/2001 | Chow et al. | |
| 6,649,669 B2 | 11/2003 | Dickens | |
| 6,797,767 B2 * | 9/2004 | Stannard ................ | A61K 6/887 524/559 |
| 7,041,709 B2 | 5/2006 | Klee et al. | |
| 7,091,260 B2 | 8/2006 | Kuhn | |
| 7,189,263 B2 | 3/2007 | Erbe et al. | |
| 7,449,499 B2 | 11/2008 | Craig et al. | |
| 7,491,694 B2 | 2/2009 | Reynolds et al. | |
| 7,727,539 B2 | 6/2010 | Laurencin et al. | |
| 7,758,693 B2 | 7/2010 | Wenz | |
| 7,767,731 B2 | 8/2010 | Chen et al. | |
| 7,879,388 B2 | 2/2011 | Clarkson et al. | |

(Continued)

FOREIGN PATENT DOCUMENTS

| | | | |
|---|---|---|---|
| EP | 2123246 A1 | 11/2009 | |
| EP | 2305205 A1 | 4/2011 | |

(Continued)

OTHER PUBLICATIONS

Arsad et al., "Synthesis and Characterization of Hydroxyapatite Nanoparticles and ?-TCP Particles," 2011 2nd International Conference on Biotechnology and Food Science, IPCBEE, vol. 7, pp. 184-188, 2011.

Chen et al., "Bond Strengths of Two Self-adhesive Resin Cements to Dentin with Different Treatments," Journal of Medical and Biological Engineering, vol. 31, No. 1, pp. 73-77, 2011.

Constantz et al., "Skeletal Repair by in Situ Formation of the Mineral Phase of Bone," Science, vol. 267, pp. 1796-1799, Mar. 24, 1995.

(Continued)

*Primary Examiner* — Matthew P Coughlin
*Assistant Examiner* — Thurman Wheeler
(74) *Attorney, Agent, or Firm* — Sunstein LLP

(57) ABSTRACT

A method of forming a stabilized calcium phosphate moiety for use in dental or biomedical applications includes providing a solution or dispersion including a calcium salt and reacting an organic phosphate having a polymerizable methacrylate or vinyl group with the solution or dispersion in order to form the calcium phosphate moiety having at least one pendant polymerizable group and at least one organic functional group, which may be the same group. A polymerizable composite system having a stabilized calcium phosphate formed according to the method is also provided.

11 Claims, 15 Drawing Sheets

(56) References Cited

U.S. PATENT DOCUMENTS

| | | | |
|---|---|---|---|
| 7,879,924 | B2 | 2/2011 | Torii et al. |
| 8,158,694 | B2 | 4/2012 | Tanaka et al. |
| 8,216,359 | B2 | 7/2012 | Lee et al. |
| 8,221,781 | B2 | 7/2012 | Rosenberg et al. |
| 8,263,048 | B2 | 9/2012 | Yang et al. |
| 8,282,396 | B2 | 10/2012 | Chow et al. |
| 8,303,967 | B2 | 11/2012 | Clineff et al. |
| 8,440,741 | B2 | 5/2013 | Sang et al. |
| 8,497,312 | B2 | 7/2013 | Matsushige et al. |
| 8,545,858 | B2 | 10/2013 | Rosenberg et al. |
| 8,551,525 | B2 | 10/2013 | Cook et al. |
| 8,557,038 | B2 | 10/2013 | Chow et al. |
| 8,609,071 | B2 | 12/2013 | Reynolds |
| 8,710,114 | B2 | 4/2014 | Rusin et al. |
| 8,728,536 | B2 | 5/2014 | Lee et al. |
| 8,796,354 | B2 | 8/2014 | Gyakushi et al. |
| 8,871,167 | B2 | 10/2014 | Aizawa et al. |
| 8,889,396 | B2 | 11/2014 | Xu |
| 8,957,126 | B2 | 2/2015 | Rusin et al. |
| 2003/0071387 | A1 | 4/2003 | Beitelshees et al. |
| 2006/0004122 | A1 | 1/2006 | Hecht et al. |
| 2007/0184035 | A1 | 8/2007 | Pugh et al. |
| 2008/0318190 | A1 | 12/2008 | Suh et al. |
| 2012/0021383 | A1* | 1/2012 | Skaria ............ C08G 18/672 433/219 |
| 2014/0050674 | A1 | 2/2014 | Tjaderhane |
| 2014/0079650 | A1 | 3/2014 | Reynolds |

FOREIGN PATENT DOCUMENTS

| | | |
|---|---|---|
| JP | 2009084200 A | 4/2009 |
| JP | 2012077009 A | 4/2012 |
| WO | 9836639 A1 | 8/1998 |
| WO | 0247572 A1 | 6/2002 |
| WO | 2010033515 A1 | 3/2010 |

OTHER PUBLICATIONS

Dhanalakshmi et al., "Synthesis and preliminary characterization of polyethylene glycol (PEG)/hydroxyapatite (HAp) nanocomposite for biomedical applications," International Journal of Physical Science, vol. 7, No. 13, pp. 2093-2101, Mar. 23, 2012.

Dorozhkin, "Amorphous Calcium Orthophosphates: Nature, Chemistry and Biomedical Applications," International Journal of Materials and Chemistry, vol. 2, No. 1, pp. 19-46, 2012.

Drouet, "Apatite Formation: Why It May Not Work as Planned, and How to Conclusively Identify Apatite Compounds," Hindawi Publishing Corporation, BioMed Research International, vol. 2013, Article ID 490946, 12 pages, 2013.

Goncalves et al., "Dental cementum reviewed: development, structure, composition, regeneration and potential functions," Braz. J. Oral. Sci., vol. 4, No. 12, pp. 651-658, Jan./Mar. 2005.

Goudouri et al., "In Vitro Bioactivity Studies of Sol-Gel Derived Dental Ceramics/Bioactive Glass Composites in Periodically Renewed Biomimetic Solution," Ashdin Publishing, Bioceramics Development and Applications, vol. 1, Article ID 0110250, 4 pages, 2011.

Grover et al., "In vitro ageing of brushite calcium phosphate cement," Biomaterials, vol. 24, pp. 4133-4141, 2003.

Grover et al., "The effect of amorphous pyrophosphate on calcium phosphate cement resorption and bone generation," Biomaterials, vol. 34, pp. 6631-6637, 2013.

Huang et al., "In vivo evaluation of poorly crystalline hydroxyapatite-based biphasic calcium phosphate bone substitutes for treating dental bony defects," J. Deni. Sci., vol. 5, No. 2, pp. 100-108, 2010.

Idrissi et al., "A novel method to synthesize nanocrystalline hydroxyapatite: Characterization with x-ray diffraction and infrared spectroscopy," IOSR Journal of Applied Chemistry, vol. 7, Issue 5, Ver. 111, pp. 107-112, May 2014.

Jefferies, "Advances in Remineralization for Early Carious Lesions: A Comprehensive Review," Continuing Education 1, Compendium, vol. 35, No. 1, 7 pages, Jan. 2014.

Kantharia et al., "Nano-hydroxyapatite and its contemporary applications," Journal of Dental Research and Scientific Development, vol. 1, Issue 1, pp. 15-19, 2014.

Oortgiesen et al., "Regeneration of the periodontium using enamel matrix derivative in combination with an injectable bone cement," Clin. Oral. Invest., vol. 17, pp. 411-421, 2013.

Sun et al., "Preparation and Properties of Nanoparticles of Calcium Phosphates With Various Ca/P Ratios," Journal of Research of the National Institute of Standards and Technology, vol. 115, No. 4, pp. 243-255, 2010.

Tomsia et al., "Biomimetic Bonelike Composites and Novel Bioactive Glass Coatings," Advanced Engineering Materials, vol. 7, No. 11, pp. 999-1004, 2005.

Tseng et al., "Polymer-assisted synthesis of hydroxyapatite nanoparticle," Materials Science and Engineering C, vol. 29, pp. 819-822, 2009.

Zhao et al., "Amorphous calcium phosphate and its application in dentistry," Chemistry Central Journal, vol. 5, No. 40, 7 pages, 2011.

International Searching Authority, International Search Report—International Application No. PCT/US2016/017255, dated Apr. 28, 2016, together with the Written Opinion of the International Searching Authority, 12 pages.

Chen, Liang et al., "Bioactive dental restorative materials: A review," American Journal of Dentistry, vol. 26, No. 4, pp. 219-227, Aug. 2013.

Al-Sanabani, Jabr S. et al., "Application of Calcium Phosphate Materials in Dentistry," International Journal of Biomaterials, vol. 2013, Article ID 876132, 19 pages, May 2013.

Spencer, Pauletie et al., "Adhesive/Dentin Interface: The Weak Link in the Composite Restoration," Ann Biomed Eng., vol. 38, No. 6, 1989-2003, 24 pages, Jun. 2010.

International Searching Authority, International Search Report—International Application No. PCT/US2017/014502, dated May 9, 2017 together with the Written Opinion of the International Searching Authority, 16 pages.

\* cited by examiner

STABILIZED CALCIUM PHOSPHATE

CROSS-REFERENCE TO RELATED APPLICATIONS

The present application is a divisional of U.S. patent application Ser. No. 14/638,289 filed Mar. 4, 2015, the disclosure of which is incorporated by reference herein in its entirety.

TECHNICAL FIELD

The present invention relates to stabilized calcium phosphate, and more specifically to stabilized calcium phosphate useful in dental and biomedical applications.

BACKGROUND ART

Calcium phosphates (CaP), such as hydroxyapatite, tricalcium phosphates and other soluble calcium phosphates (brushites) and others, have found many biomedical applications over the years. Hydroxyapatite and other calcium phosphate implants exhibit good tissue compatibility and help the formation of new bone without forming any fibrous tissues because their chemical compositions are similar to that of bone material. Recently, Varghese et al., using a mineralized synthetic matrix mimicking a CaP rich bone microenvironment, demonstrated the beneficial role of CaP biomaterials in bone repair and the role of calcium and phosphate ions in bone physiology and remineralization. In bone tissue engineering, calcium phosphates have been applied as filling materials for bone defects and augmentation, artificial bone graft material, and in prosthesis revision surgery. Its high surface area leads to excellent osteoconductivity and resorbability providing fast bone in-growth. In dentistry, dentifrices and varnishes containing calcium ions, phosphate ions and fluoride ions are being used for the remineralization of dentinal tissues. Calcium containing cements find use as structural supports in orthopedic and dental applications. In a recent study, Schumacher et al. developed biologically active restorative materials that may stimulate the repair of tooth structure through the release of cavity-fighting components including calcium and phosphate. They disclosed the use of amorphous calcium phosphate (ACP) as a bioactive filler encapsulated in a polymer binder. Calcium and phosphate ions released from ACP composites, especially in response to changes in the oral environment caused by bacterial plaque or acidic foods, can be deposited into the tooth structures as an apatite mineral, which is similar to the hydroxyapatite found naturally in teeth. The ACP has the properties of both a preventive and restorative material. This encourages its use in dental cements, sealants, composites, and, more recently, orthodontic adhesives. ACP-filled composite resins have been shown to recover 71% of the lost mineral content of decalcified teeth. Though ACP has been used in some dental applications, its use in dental restorative materials is very limited due to its stability. In contact with water, ACP turns into hydroxyapatites.

There has been a lot of research on the development of calcium phosphates and hydroxyapatites for various biomedical applications. A calcium phosphate useful in biomedical applications should possess at least the following properties: (1) it should be chemically biocompatible like hydroxyapatite; (2) it should be in soluble form to permit resorption so that the patient's own bone can replace the foreign hydroxyapatite; and (3) it should be able to mix into a matrix formulation without losing its chemical integrity, its bioactivity and its ability to release beneficial ions, such as calcium and phosphate.

A number of researchers have reported on the production of crystalline hydroxyapatites. These involve either solution precipitation followed by sintering at very high temperatures such as (800-1200° C.) (LeGeros, Calcium Phosphates in Oral Biology, Karger Pub, NY, 1991) or solid state acid base reaction of primarily crystalline calcium phosphates. These methods generate highly crystalline phases with limited solubility.

The formation of calcium phosphate minerals by the reaction of phosphoric acid and calcium source in the presence of a base and hydroxyapatite crystals has been reported by Contstantz in U.S. Pat. No. 4,880,610. He also studied the use of powdered acid salts to improve the workability in U.S. Pat. No. 5,053,212, and the use of a mixture of calcium phosphate salts and carbonates in sodium phosphate solution to generate a calcium phosphate material with substantially greater crystallinity than in naturally occurring bone.

Palmer et al. in U.S. Pat. No. 4,849,193 reported the formation of crystalline hydroxyapatite powder by reacting an acidic calcium phosphate solution with a calcium hydroxide solution to generate an amorphous hydroxyapatite powder. These amorphous powders were then dried and sintered at 700° C.-1100° C. to generate high crystalline hydroxyapatite. Recently, Arsad et al. reported the synthesis and characterization of hydroxyapatites formed by the reaction of calcium chloride and a phosphate source. More recently other wet methods have been developed for the synthesis of nanosized hydroxyapatite crystals from calcium nitrate and sodium phosphate salts.

Though the preparation of crystalline calcium phosphate and its use in dental cements has been reported by Brown et al., Tung et al. were the first to disclose the use and application of standard amorphous calcium phosphate for the remineralization of teeth. The amorphous calcium phosphates, incorporated in the chewing gum, released soluble calcium and phosphate ions and formed crystalline hydroxyapatite in oral conditions. The effective application of ACP is limited in restorative or regenerative dentistry and is limited due to its instability in and incompatibility with monomers containing acidic functional groups.

Various researchers have attempted to stabilize and protect calcium phosphate particles with polyethylene glycol and sugar alcohols. These protected calcium phosphates have efficiently released calcium and phosphate ions and helped in the remineralization of dentin tooth surfaces. Thermodynamically stabilized calcium phosphate clusters, using phosphoprotein molecules at a pH in the range of 6-7.2 have been reported by Holt et al. in U.S. Pat. No. 7,060,472. Stabilization using phosphopeptides at pH above 7 is reported by Reynolds et al. in U.S. Pat. No. 7,312,193. Pugh et al. in U.S. Pat. No. 6,585,992 reported a synthetic biomaterial compound based on stabilized calcium phosphate and, more particularly, the molecular, structural and physical characterization of calcium phosphate compounds stabilized with boron and silicon. Amsden et al. in U.S. Pat. No. 8,529,933 reported the synthesis of biphasic calcium phosphate cement for drug delivery that incorporated biopolymer carriers for the site-specific introduction of natural or synthetic compounds to influence bone repair and/or patient recovery. Pugh et al. in U.S. Pat. Appl. No. 2007/0184035 described the artificial stabilization of calcium phosphate phases developed by the conversion of a hydroxyapatite substance into insolubilized and stabilized tricalcium phosphate. They also described applications for this material in medical diagnostics for the assessment of abnormal bone cell activity and for medical therapeutics, including bone and dental tissue replacement and repairs and for ex vivo bone graft tissue engineering. Reynolds et. al. in U.S. Pat. Appl. No. 2014/0079650 disclosed the synthesis of stabilized calcium phosphate synthesized below a pH of 7 and its applications in dental remineralization including in formulations such as mouth wash and chewing gum. Rusin et al. in U.S. Pat. No. 8,790,707 described the surface modification of calcium phosphate particles with a sugar alcohol and/or at least one glycerophosphoric acid compound. They also described oral care compositions comprising surface treated calcium phosphate particles. Yang et al. in U.S. Pat. No. 8,263,048 described calcium phosphate particles surface treated with sugar alcohols and their application in oral formulation.

Jia in U.S. Pat. No. 6,270,562 disclosed a dental composition with a glass filler material having bonded surface modifying particles, including fluoro-alumino silicate glasses and a composition with resins, glass fillers and treated glass fillers. Other concepts disclosed include the preparation of amorphous calcium phosphate particles precipitated on zirconium, titanium and silica particles and compositions including amorphous calcium phosphate supported with filler particles and resins. Though these methods would generate amorphous calcium phosphate particles, their stability still has not been improved and their application in combination with acid containing adhesive monomers is limited.

Another drawback of calcium phosphate cements is their low mechanical properties. Hydroxyapatite as a bulk solid does not have the necessary mechanical properties, such as strength or stiffness, to be used in load bearing applications. While much has been learned about the structure and growth of bone tissue due to modern microscopy, no reliable method of synthesizing this structure has been developed.

Experience with calcium-based implants for the replacement of skeletal tissue has also existed for many years. Most of these implants have been in the form of prefabricated, sintered hydroxyapatite in either granule or block forms. These preparations have several drawbacks, including a limited ability to conform to skeletal defects, particularly in the case of blocks, inadequate structural integrity of granules (which do not bond together), and difficulty in modeling the implant to the shape of missing skeletal tissue with both blocks and granules. The block form of hydroxyapatite provides structural support, but among other complications, must be held in place by mechanical means, which greatly limits its use and its cosmetic results. It is also very difficult to saw a shape such that it fits the patient's individual defect. The granular form produces cosmetically better results, but has a very limited structural stability and is difficult to contain during and after a surgical procedure. In general, all of these products are ceramics, produced by high temperature sintering, and are not individually crystalline, but rather have their crystal boundaries fused together. These ceramic-type materials are in general functionally biologically non-absorbable (having an absorption rate generally not exceeding on the order of 1% per year). For example, both apatite and brushite cements are commercially available, but their usefulness in the construction of bone defects and their behavior in the bone defect are quite different due to their difference in the resorption. Brushite cements are resorbed much faster compared to apatite cements. The difference is caused by the compositional difference in the final products. Therefore, the final product of apatite cement is apatite and the final product of brushite cement is brushite The patent literature does, however, describe at least one class of calcium phosphate compositions which are precursors for the formation of hydroxyapatite. These compositions offer good remineralization potential as slurries and are biologically compatible, self-setting (self-hardening), and substantially resorbable (biodegradable) with bone replacement as cements when implanted in contact with living bone tissue. For example, U.S. Pat. Nos. Re. 33,221 and Re. 33,161 to Brown and Chow teach preparation of calcium phosphate remineralization compositions and finely crystalline, non-ceramic, gradually resorbable hydroxyapatite cement based on the same calcium phosphate composition. However, these cements lack the mechanical strength required for medical implants where high load strength is required. Somewhat similar, and in certain instances potentially identical products, are described in U.S. Pat. Nos. 5,053,212, 4,880,610, 5,129,905, 5,047,031, and 5,034,059 to Constantz and others, although the use of non-traditional chemical terminology in the latter patents makes interpretation of them and comparison of them with the prior work of Brown and Chow difficult.

SUMMARY OF EMBODIMENTS

In accordance with one embodiment of the invention, a method of forming a stabilized calcium phosphate for use in dental or biomedical applications includes providing a solution or dispersion including a calcium salt and reacting an organic phosphate having a polymerizable methacrylate or vinyl group with the solution or dispersion in order to form a calcium phosphate moiety having at least one pendant polymerizable group and at least one organic functional group.

In some embodiments, the at least one pendant polymerizable group and the at least one organic functional group are the same group. The calcium salt may include calcium chloride, calcium hydroxide, and/or calcium nitrate. The organic phosphate having the polymerizable methacrylate or vinyl group may include bis[2-(methacryloyloxy)ethyl] phosphate (CAS #32435-46-4, hereinafter sometimes referred to as "Bis 2"), methacryloxy ethyl phosphate, glycerol dimethacrylate phosphate, glycerol monomethacrylate phosphate, triethyleneglycol methacrylate phosphate, methacryloyloxy propyl phosphate, methacryloyloxy hexyl phosphate, vinyl phosphonic acid, allyl phosphonic acid, polyethylene glycol methcrylate phosphate, methacrylated aminomethyl phosphonic acid, methacrylate esters of glycerol phosphate, and/or polycaprolactone methacrylate phosphate. The method may further include adding one or more inorganic phosphate sources to the organic phosphate to form a mixture. The reaction may include reacting the mixture with the solution or dispersion in order to form the calcium phosphate moiety. The one or more inorganic phosphate sources may include phosphoric acid or its salt, ammonium phosphate, and/or pyrophosphoric acid or its salt. The phosphoric acid or its salt may include sodium salt of phosphoric acid. The solution may include the calcium salt solubilized or dispersed in deionized water. Reacting the organic phosphate with the solution may include hydrolyzing the polymerizable methacrylate in order to form the calcium phosphate moiety. Embodiments may include a stabilized calcium phosphate formed according to the method.

In accordance with another embodiment of the invention, a polymerizable composite system for use in dental or biomedical applications may include stabilized calcium phosphate formed according to the method above, and one or more monomers selected from the group consisting of acidic monomers, hydrophilic monomers, and/or hydrophobic monomers.

In some embodiments, the one or more monomers may include urethane dimethacrylate, bis[2-(methacryloyloxy) ethyl] phosphate, 1,6 hexamethylene dimethacrylate, trimethylol propane triacrylate, hydroxyethyl methacrylate, polyethylene glycol methacrylate, triethylene glycol dimethacrylate, polyethylene glycol dimethacrylate, polylactic acid methacrylate, polycaprolactone methacrylate, bisphenol A glycidyl methacrylate, bisphenol A glycidyl diacrylate, bisphenol A ethoxylate dimethacrylate, bisphenol A dimethacrylate, and/or bisphenol A diglycidyl ether. The system may further include one or more polymers and/or oligomers. The one or more polymers and/or oligomers may include oligomeric polybutadiene diurethane dimethacrylate. The system may further include a photoinitiator system. The photoinitiator system may include camphorquinone and an amine or a triphosphene oxide. The system may further include a non-reactive filler. The non-reactive filler may include silica, barium glass, strontium glass, quartz, and/or barium sulfate. The system may further include a self-curing system having a reducing agent and an oxidizing agent. The system may further include a dual cure system.

BRIEF DESCRIPTION OF THE DRAWINGS

The foregoing features of the invention will be more readily understood by reference to the following detailed description, taken with reference to the accompanying drawings, in which.

DESCRIPTION OF ILLUSTRATIVE EMBODIMENTS

Figure 1:
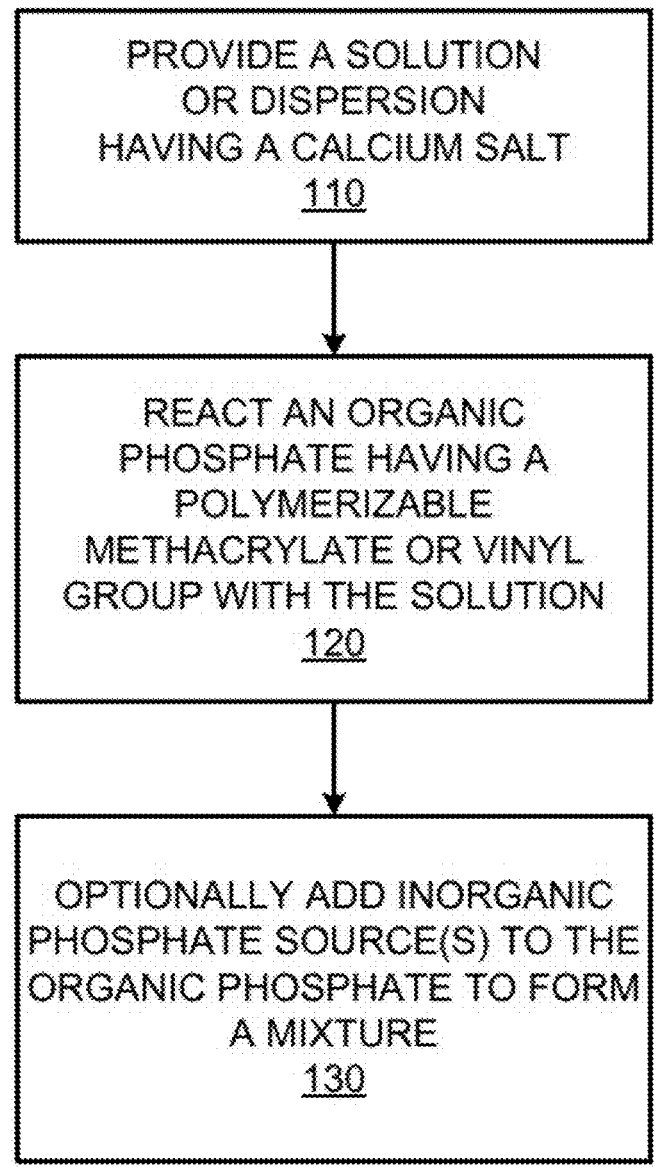
FIG. 1 is a flow chart showing a method of forming a stabilized calcium phosphate for use in dental or biomedical applications according to embodiments of the present invention.

Embodiments of the present invention provide stabilized, encapsulated, poorly crystalline hydroxyapatite and amorphous calcium phosphate particles formed by the in situ process of using phosphate containing monomers in stoichiometric amounts, with respect to calcium ions, as the phosphate source along with an optional phosphoric acid. Poorly crystalline hydroxyapatite is defined as hydroxyapatite with high lattice disorder and low crystallite sizes, which in some embodiments is referred to herein as transitional methacrylate encapsulated calcium phosphate. The low crystallite sizes and high lattice disorders are formed due to the presence of external molecules. The preparation of low crystalline hydroxypatites with the addition of nonphosphate bearing organic molecules has been reported. Poorly crystalline hydroxyaptites show higher solubility and better resorption than highly ordered crystalline hydroxyapatites. In embodiments of the present invention, however, an organic phosphate having a polymerizable methacrylate or vinyl group, such as bis[2-(methacryloyloxy)ethyl] phosphate (referred to herein as "Bis 2"), CAS #32435-46-4, a phosphate containing methacrylate ester reagent, acts as the phosphate source and also regulates the crystallinity of hydroxyapatite formed by creating lattice disorders. The calcium phosphate formed includes at least one pendant polymerizable group and at least one organic functional group, which, in some embodiments, may be the same group. The organic monomeric group encapsulates, stabilizes and regulates the calcium phosphate formed. Thus, the calcium phosphate formed according to embodiments of the present invention exhibits higher stability and good resin integration owing to the pendant polymerizable groups. Some embodiments include the use of polymerizable and non polymerizable phosphate reagents as the source of phosphate ions. Details of illustrative embodiments are discussed below.

The hydroxyapatite and stabilized calcium phosphate formed according to embodiments of the present invention described herein are characterized by many important advantages as compared with traditional hydroxyapatite materials explained in the prior art or commercially available, even though both materials fall within the same general class of hydroxyapatite. For example, the synthesized stabilized calcium phosphate formed according to embodiments of the present invention exhibits high stability and thus can be used in a polymerizable resin system containing acidic monomers, hydrophilic monomers and/or hydrophobic monomers. The modified calcium phosphate described in embodiments of the present invention includes pendant polymerizable groups and hence provides good adhesion to dentin, metallic and glass surfaces. In addition, embodiments of the synthesized modified calcium phosphate materials formed may be used as bioactive filler for dental restorative and bone substitute materials. As used herein, bioactive material refers to material which releases beneficial ions, such as calcium and phosphates, and is able to regenerate and heal bones and dentin. A biocomposite refers to a composite which contains bioactive material and has the ability to release and transport bioactive ions and is able to induce bioactivity.

FIG. 1 is a flow chart showing a method of forming a stabilized calcium phosphate for use in dental or biomedical applications according to embodiments of the present invention. In step 110, a solution including a calcium salt is provided. The calcium salt may be dissolved in water, e.g., deionized water, or other suitable solvent. The calcium salt precursor used may be selected from various calcium sources, such as calcium chloride dehydrate, calcium hydroxide, calcium nitrate, and/or a mixture of calcium containing sources. In one embodiment, the calcium salt is calcium hydroxide and the calcium to phosphate ratio is about 1.67.

In step 120, the solution is reacted with an organic phosphate having a polymerizable methacrylate or vinyl group in order to form a calcium phosphate having at least one pendant polymerizable group and at least one organic functional group. The organic phosphate source may include Bis 2, methacryloxy ethyl phosphate, glycerol dimethacrylate phosphate, glycerol monomethacrylate phosphate, triethyleneglycol methacrylate phosphate, methacryloyloxy propyl phosphate, methacryloyloxy hexyl phosphate, glyceryl phosphate, polyethylene glycol mono phosphate, triethylene glycol monophosphate, triethyl phosphate, inositol, polyethylene glycol methcrylate phosphate, methacrylated aminomethyl phosphonic acid, methacrylate esters of glycerol phosphate, polycaprolactone phosphate, or combinations thereof and vinyl functional phosphates may include vinyl phosphonic acid, and/or allyl phosphonic acid.

In step 130, inorganic phosphate source(s) may be added to the organic phosphate to form a mixture, and then the mixture may be reacted with the solution in order to form the calcium phosphate having at least one pendant polymerizable group and at least one organic functional group. The inorganic phosphate sources may include phosphoric acid, sodium salt of phosphoric acid, ammonium phosphate, pyrophosphoric acid and their salts or a combination thereof.

Embodiments include a novel synthetic methodology for the preparation of these stabilized modified calcium phosphates. The structure and formation of the stabilized calcium phosphates depend on various parameters, such as the molar concentration and the ratios of the calcium and phosphate sources and the pH of the reaction medium and as well as the temperature of the reaction medium. The calcium and phosphate ions form a varying number of salts such as mono calcium phosphates, dicalcium phosphates, tricalcium phosphates, tetracalcium phosphates based on the synthesis procedures such as ionic strength, pH and temperature. Hydroxyapatite is the most stable form of the calcium salts at physiological pH or above. The biological activity of the calcium salt in the formation of bone regeneration is also different and these are determined by the resorption of calcium and phosphate. If the calcium phosphate is more soluble, then the resorption of the ions is more gradual and the bone growth is faster. For example, both apatite and brushite cements are commercially available, but their usefulness in the construction of bone defects and their behavior in the bone defect are quite different due to their difference in resorption. Brushite cements are resorbed much faster compared to apatite cements.

The novel materials formed according to embodiments of the present invention have the advantage of effective applications in acid based formulations, such as in adhesive and restorative dentistry. Therefore, the novel stabilized calcium phosphates may be used in polymerizable composite systems along with one or more acidic monomers, hydrophilic monomers, and/or hydrophobic monomers. Polymerizable compounds with acid functionality and double bonds that may be used with the novel stabilized calcium phosphates include, for example, Bis 2, glycerol phosphate dimethacrylate, glycerol phosphate monomethacrylate, ethylene glycol methacrylate phosphate, triethyleneglycol methacrylate phosphate, polyethyleneglycol methacrylate phosphate, polycaprolactone methacrylate phosphate, methacryloyloxy propyl phosphate, and/or methacryloyloxy hexyl phosphate. Methacrylated pyromellitic acid, methacryloyloxy succinic acid, and methacryloyoloxy maleic acid are ethylenically unsaturated compounds with acid functionality having one COOH group or P—OH group may also be used. In some embodiments, the stabilized calcium phosphates are stabilized by the presence of alkyl methacrylate groups.

Restorative dental composites, including dental adhesives, often contain ethylenically unsaturated compounds with acid functionality, which includes monomers, oligomers and polymers having ethylenic unsaturation and/or acid precursor functionality. Prior art amorphous calcium phosphates are not stable in acidic conditions or in the presence of water. Therefore, resin formulations using such prior art calcium phosphates may result in the formation of unwanted salt formations with the acid functionality, which hinders their effective application.

The presence of a plurality of methacrylated groups in the novel materials provides better integration with organic resin systems and has the ability to covalently link to the resin matrix while taking part in polymerization. The use of the present stabilized calcium phosphate material as a filler in dental applications as well as bio composites results in composites with better mechanical strength which can be used in load bearing applications. The compressive strengths and tensile strength of these composites are much higher than that of prior art hydroxyapatite composites. Suitable photopolymerizable compositions of this type may include monomers which contain polymerizable ethylenic groups. Methacrylic acid esters or methacrylic acid or acrylic acid esters of various functional molecules are an example of such compounds. The polymerizable composite systems may further include one or more polymers and/or oligomers, such as oliogomers which contain free radically polymerizable double bonds, which may result in polymers with enhanced toughness and flexural properties. Compositions containing such oligomers which increase the toughness of polymeric composites are described in U.S. Pat. No. 8,292,625 to Skaria and Berk, incorporated by reference herein in its entirety. The polymerizable compositions, in addition to free radically active monomers or oligomers, may also contain suitable photo initiators, for photopolymerizing the polymerizable compositions. As known by one skilled in the art, photoinitiator systems may include a photosensitizer compound such as camphorquinone and/or an activator, such as an amine, e.g., a tertiary amine.

Chemically polymerizable compositions which can be used as restorative dental composites for the restoration of dental tissues, as a biocomposite for the regeneration of bones, or as cements with remineralizing abilities may include ethylenically unsaturated monomers or polymers with the present stabilized calcium phosphate material as a filler and may also include a suitable redox cure system. As known by one skilled in the art, self-cure or chemical cure resin systems have compositions with a reducing agent that react with an oxidizing agent to produce free radicals capable of initiating polymerization of the resin system. Such self-cure or chemical cure systems work independently regardless of the presence of light and hence may be defined as dark polymerization or autopolymerization systems. Bone cement formulations generally work under dark conditions and these sorts of polymer compositions are very useful as bone cements. Suitable oxidizing agents which may be used in the present polymerizable compositions may include peroxides such as benzoyl peroxide, cumene hydroperoxides, t-butyl peroxide, amyl peroxide, valeryl peroxide or lauroyl peroxide. Suitable reducing agents that may be used in the present polymerizable compositions for dental or biomedical composites may include amines, especially tertiary amines, such as hydroyethyl paratoluidine, 4-tert-butyl dimethyl aniline, thioureas such 1-acetyl thiourea, tetraethyl thiourea, 1,1 dibutyl thiourea and barbiturates such as barbituriic acid, 2-dimethylaminoethyl methacrylate or phenyl-barbiturate. The amount of the reducing agents and oxidizing agents used in the present resin compositions should be effectively controlled to regulate the rate of polymerization or hardening of the material in order to have enough workability and applicability. Dual curable resin composites containing acid monomers with glass and silica fillers and their applications in restorative dentistry is disclosed in U.S. Pat. Nos. 6,797,767 and 7,371,782 to Stannard and Berk, incorporated by reference herein in its entirety. As known by one skilled in the art, a dual cure system may be cured by light or left to autopolymerize after mixing, or both.

The stabilized calcium phosphate materials formed according to embodiments of the present invention have pendant double bonds. Due to the presence of the double bonds, the present materials provide a methacrylate-encapsulated transitional calcium phosphate coating on a number of substrates in some embodiments. For example, the type of substrates may include bone implants, such as titanium implants, steel implants and composite implants which do not possess any or little bioactivity. In this case, the coating formulation may contain other monofunctional monomers such as hydroyethyl methacrylate, polyethylene glycol methacrylate or other functional monomethacrylates or multifunctional methacrylates such 1,6 hexamethylene dimethacrylate, triethylene glycol dimethacrylate, Bis 2, or polyethylene glycol dimethacrylate or a biodegradable monomer system, such as polylactic acid methacrylate or polycaprolactone methacrylate.

The cement formed with the present stabilized calcium phosphate was designed to be biocompatible, to have broad applications, and to offer benefits in the medical, orthopedic, dental, and veterinary fields. For example, presently available prior art bone cements typically come as a kit containing multiple components that require the medical practitioner to be familiar with the steps and precautions of preparing such cements and to be able to mix the reactants that form the cement in a time-sensitive manner during its use. In contrast, the calcium phosphate cement formed according to embodiments of the present invention is very easy to apply and can be set on demand (e.g., using photopolymerization) or can be cured using a dark polymerization process by mixing the composition and/or by injecting the cement through mixer tips. The setting rate can be adjusted for various end uses and may be quite rapid, if desired. In addition, the hydroxyapatite cement formed with the present stabilized calcium phosphate is biocompatible, and the resin composition resulted in biocomposites with high mechanical strength and toughness.

Finally, the present stabilized calcium phosphate and the polymerizable composite systems using the novel materials can release beneficial calcium and phosphate ions and can induce the crystallization of hydroxyapatite crystals and/or induce bone growth when injected in rat femurs/tibias. The cement actually promotes the growth of living bone into the implant. This osteo-integration of the cement with the surrounding bone causing the variable replacement of the implant with living bone over time results in permanent fusion and further structural stability. The in-vitro evaluation of the present material demonstrates the ability of the bioactivity of the compositions to induce the crystallization of hydroxyapatite in phosphate buffered saline. The stabilized calcium phosphate materials release beneficial calcium and phosphate ions and induce the precipitation of HAP crystals on the surface. Basically, the cement formed with the present stabilized calcium phosphate is regarded by the body as a native material; it triggers no significant or sustained inflammatory response, and no foreign body giant cell reaction. The present cement is nontoxic. The stabilized calcium phosphate formed according to embodiments of the present invention have the structural characteristics of a biomaterial, having the ability to bond to bone and dentin owing to its bioactivity. These materials can also bond to resin matrixes due to the presence of the polymerizable double bonds.

EXAMPLES

A set of experiments were run to prove the viability of the stabilized calcium phosphate formed according to embodiments of the present invention. In the following examples, the solubility of the materials was studied in 0.2N sodium chloride solution. The solubility was determined by calculating the amount of calcium and phosphate ions in the solution by spectrophotometry. Fourier Transform Infrared (FTIR) spectroscopy of the powdered samples and polymer specimens were taken on a Nicolet IR 200 (ThermoFischer) machine in total attenuation reflective (ATR) mode. The samples were scanned in the spectral range of 4000-400 $cm^{-1}$. Samples were prepared for X-ray diffraction (XRD) analysis by light hand-grinding in an agate mortar and pestle with the resulting powders packed into a 0.4 mm deep depression in a glass slide (average irradiated area is approximately 1 $cm^2$). The samples were then step-scanned from 5-70° 2θ (0.03°/0.7 seconds per step) using a Rigaku MiniFlex, variable slit, diffractometer equipped with a simple nickel filter and scintillation detection system and a Cu-target X-ray tube operating at 30 kV/15 mA. The calcium phosphate compounds were identified using automated search/match routines comparing the resulting diffraction patterns with those of standard compounds in X-ray diffraction databases provided by Inorganic Crystal Structure Database (ICSD) and the International Centre for Diffraction Data (ICDD). For the stability studies of the stabilized calcium phosphate powders, 0.5 g of the powders were suspended in an alcoholic solution of Bis 2 (2 g Bis 2 dissolved in 10 g ethanol) for 24 h at 37° C. and then filtered, washed and dried. Similarly, 0.5 g of the powders were stored in 10 mL sodium bicarbonate solution at pH 9.0 at 37° C. for 24 h. The powders were filtered, washed and dried. The powders were subjected to XRD and FTIR analysis.

For the calcium and phosphorous ion release, polymer discs of approximately 1 mm thickness and 15 mm diameter were fabricated on a silicon mold by irradiating the resin mix with visible light for 40 sec on each side of the specimen. The discs were then stored in distilled water at 37° C. and the solution was changed periodically and the ion content measured spectrophotometrically or by plasma induced atomic absorption spectroscopy. The amount of ions released from the polymer discs were then calculated and expressed as wt./wt. of polymer disc. The compressive strength of the specimens was measured according to the ISO 4049 standard. Specimens of 4 mm×8 mm (diameter× length) were fabricated in a polypropylene mold and light cured (Demetron, Kerr) for 40 sec on both sides. The bottom and upper surfaces of the specimens were polished to get a flat surface and the specimens were then placed in water at 37° C. for 14 h. The compressive strengths were measured using an Instron Universal tester (Instron Corp. Model 1011, Canton, Mass.) with a 5 KN load cell and at a cross head speed of 1 mm/minute. The results are reported for the average of six specimens and are given as MPa.

The bioactivity of the composite materials was studied in vitro. Disc-shaped slugs, 4 mm thick and 5 mm diameter, were prepared by photopolymerizing the resin in a polypropylene mold for 40 sec on each side. The specimens were removed and polished on 200 Grit SiC paper. The specimens were then hung vertically in 10 mL phosphate-buffered saline (PBS) for specified times. The specimens were removed and the buffer washed thoroughly with distilled water to remove adhering foreign ions on the surface. The specimen surfaces were then subjected to scanning electron microscope (SEM) imaging and Energy-dispersive X-ray spectroscopy (EDS) analysis. Translucency and Opacity studies of one millimeter discs of the material in a resin matrix at 50% filled with the present stabilized calcium phosphate were sufficiently transparent to permit reading of text below.

Example 1—Control Experiment

The preparation of hydroxy apatite according to U.S. Pat. No. 4,849,193 to Palmer et al. was done as a control sample. Specifically, 24 g. of calcium hydroxide powder was dispersed in 300 mL deionized water and was stirred vigorously. To this solution, 52 mL phosphoric acid 85% (89.17 g) in 100 mL distilled water was added slowly. The calcium hydroxide reacted with phosphoric acid and formed a clear solution with a pH of about 2.0. The stirring was further continued for another 30 min. The solution was labeled as Solution C.

Figure 2:
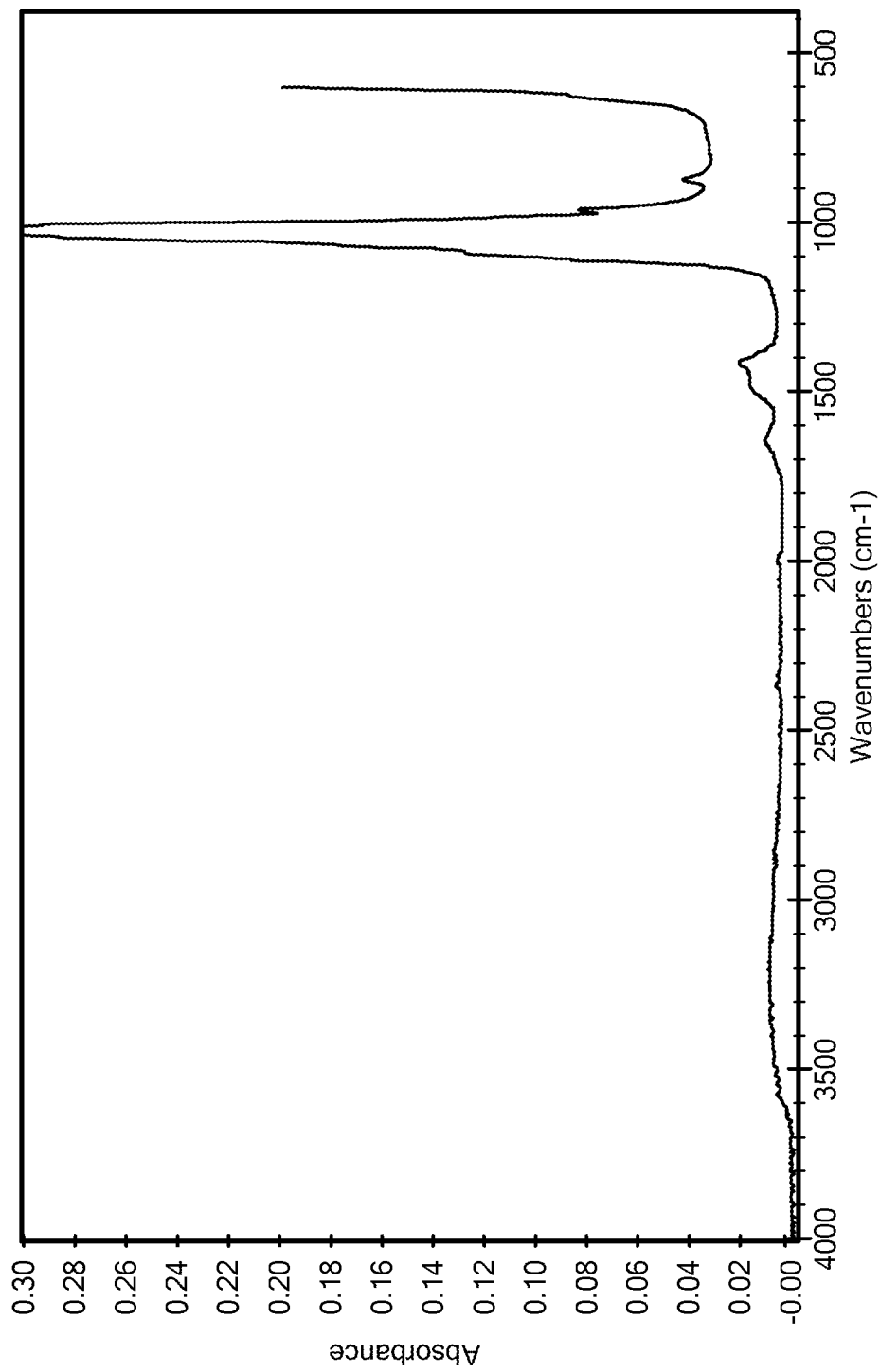
FIG. 2 is a graph showing an FTIR (ATR) spectrum of hydroxyapatite formed according to the prior art.
Figure 3:
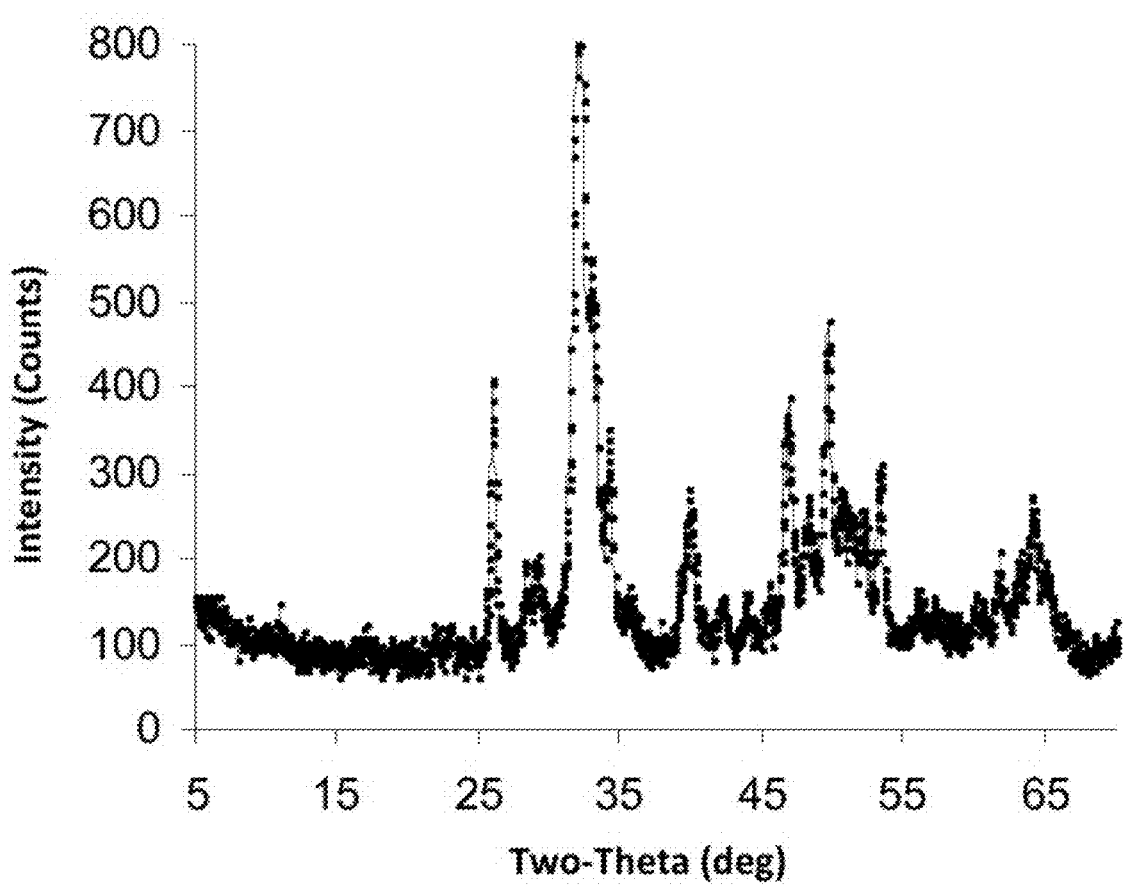
FIG. 3 is a graph showing an XRD pattern of hydroxyapatite formed according to the prior art.

In a 2 L beaker, 78 g of Ca(OH)$_2$ was dispersed in 600 mL distilled water. To this solution, Solution C was added gradually under constant and vigorous stirring. After complete addition of Solution C to the Ca(OH)$_2$ dispersion, the stirring was further continued for 6 h. The pH of the solution was about 11.5-12.0. The dispersion was decanted and further dried on a glass tray and warmed at about 50° C. The Fourier transform infrared spectroscopy (FTIR) spectrum of the hydroxyapatite synthesized by Palmer's method is shown in FIG. 2. The FTIR spectrum showed the characteristic peak related to standard hydroxyapatites and did not show any characteristic peaks for the ester bond (C=O) at 1720 cm$^{-1}$ or a vinyl (C=C) bond stretching at 1642 cm$^{-1}$. As shown in FIG. 3, the XRD pattern shows a characteristic pattern related to crystalline hydroxyapatite and the diffraction peaks are narrower compared to the diffraction peaks of the samples formed according to Examples 2, 6, and 8 (discussed below). Diffraction peak intensity and width are greatly affected by crystallite size and lattice order. Highly ordered crystallites are uniformly spaced and exhibit sharp peaks compared to smaller crystallites. Thus, the sharp and more intense peaks observed for hydroxypatite formed by Palmer's method showed that the hydroxypatite is very crystalline.

Example 2—Preparation of Stabilized Methacrylate-Encapsulated Transitional Calcium Phosphate IA—50%

The synthesis of stabilized calcium phosphate according to embodiments of the present invention was done using calcium hydroxide, Bis 2 and phosphoric acid with a modified procedure from that reported in U.S. Pat. No. 4,849,193 by Palmer et al. In this case, 24 g. of calcium hydroxide powder was dispersed in 300 mL deionized water and was stirred vigorously. To this solution, a mixture of phosphoric acid (45 g) and 75 g Bis 2 in 100 mL distilled water was added slowly. The calcium hydroxide reacted with phosphoric acid and Bis 2 and formed a clear solution. The pH of the solution was about 3. The stirring was further continued for another 30 min. The solution was labeled as Solution C.

Figure 4:
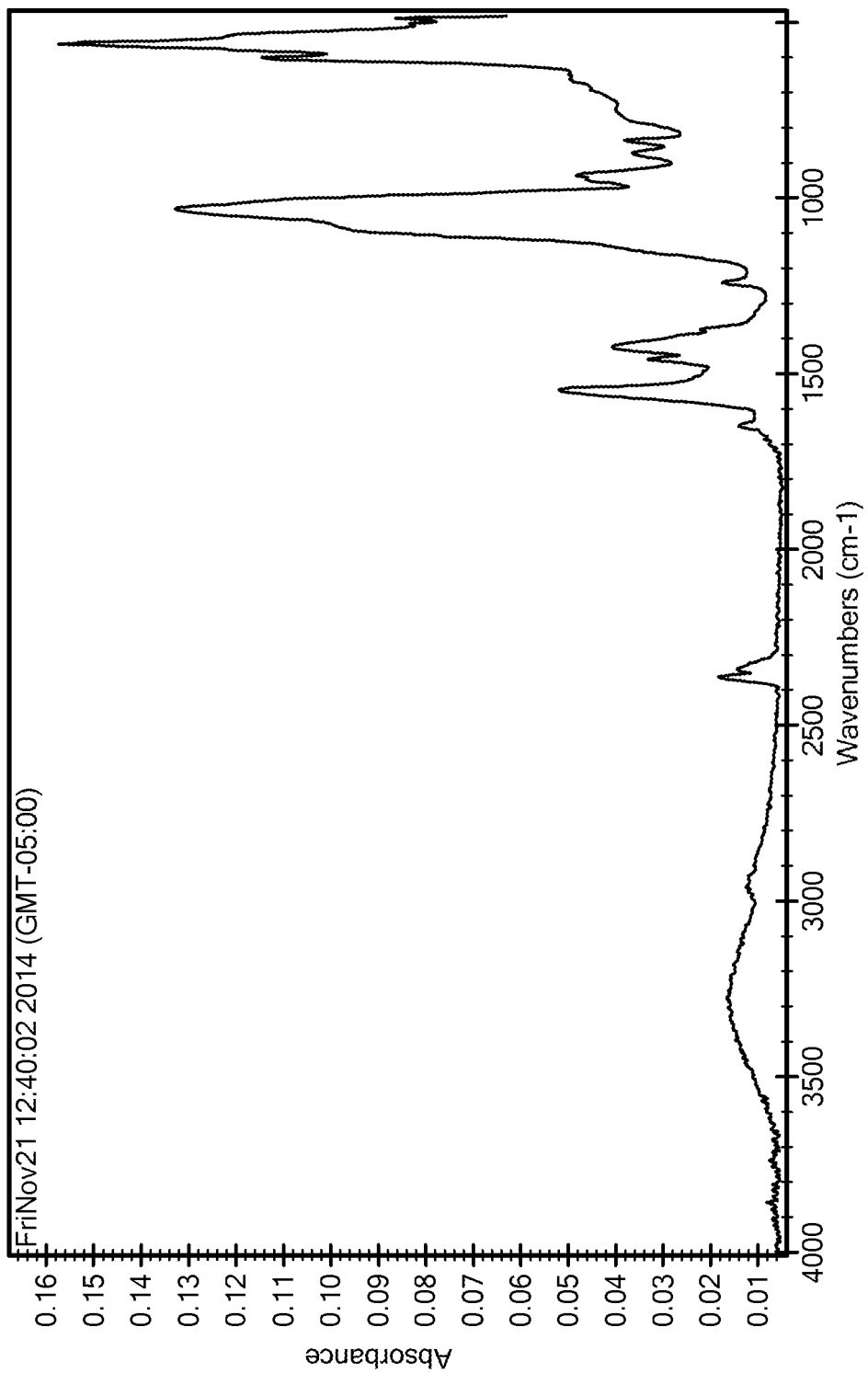
FIG. 4 is a graph showing an FTIR (ATR) spectrum of stabilized calcium phosphate—IA made from $Ca(OH)_2$/phosphoric acid and Bis 2 formed according to embodiments of the present invention.
Figure 5:
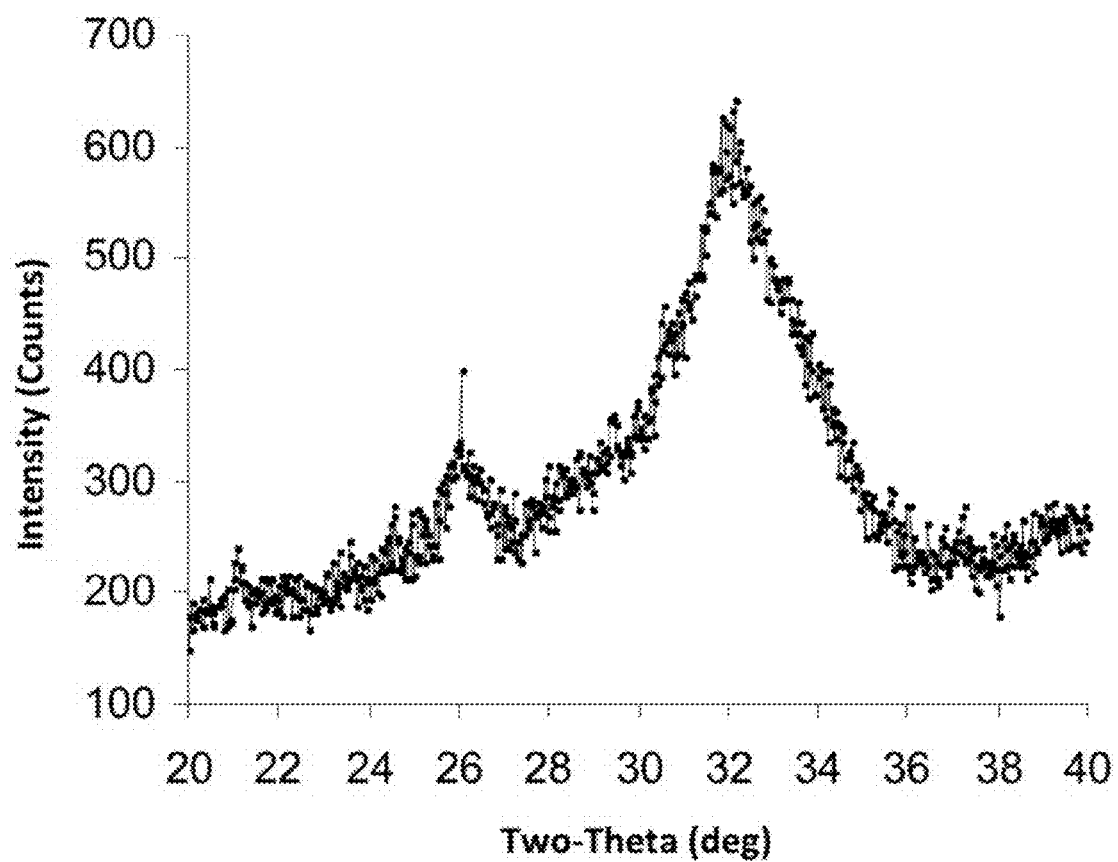
FIG. 5 is a graph showing an XRD pattern of stabilized calcium phosphate—IA made from $Ca(OH)_2$/phosphoric acid and Bis 2 formed according to embodiments of the present invention.
Figure 6:
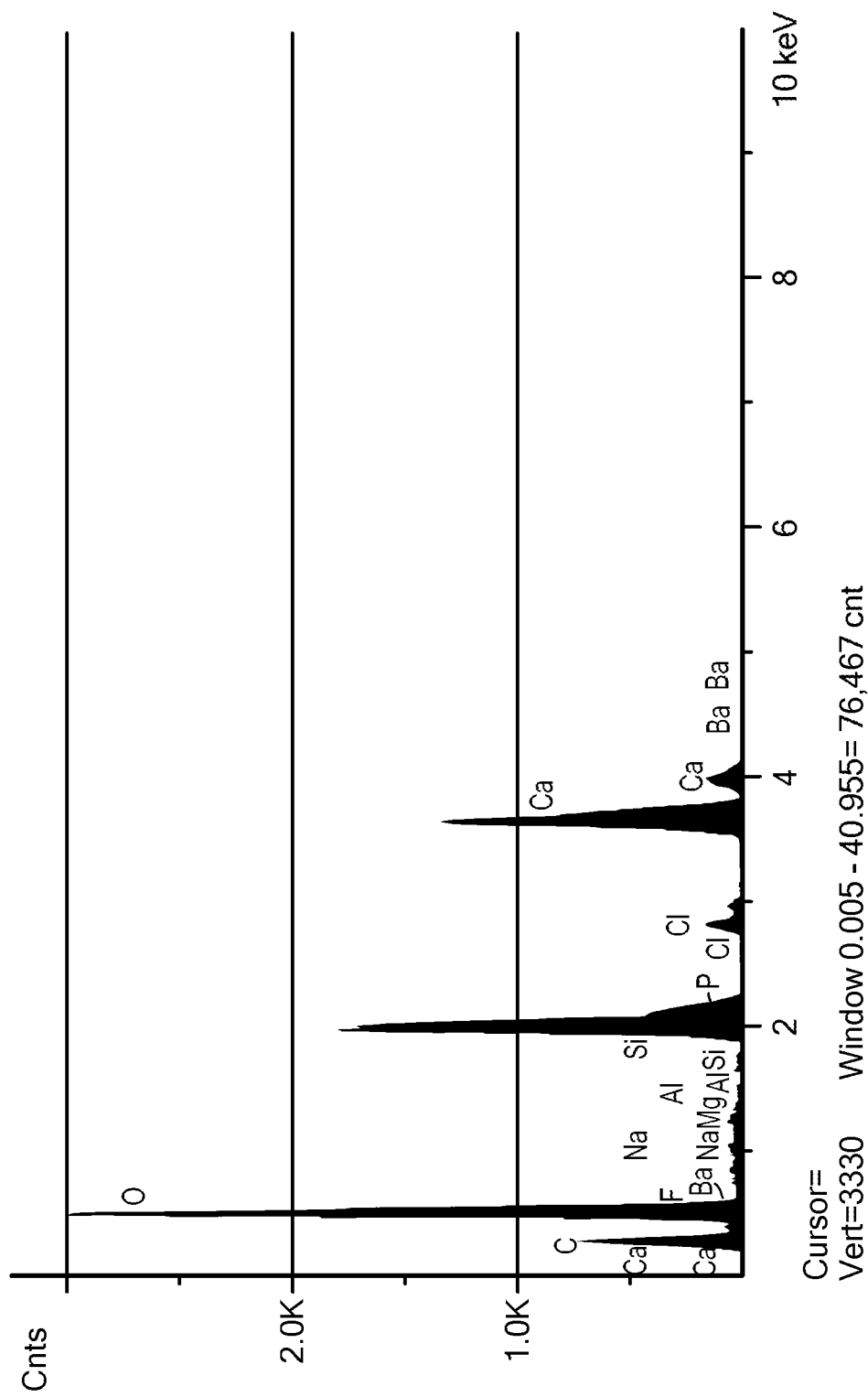
FIG. 6 is a graph showing an EDS analysis of stabilized calcium phosphate—IA made from $Ca(OH)_2$/phosphoric acid and Bis 2 formed according to embodiments of the present invention.

In a 2 L beaker, 78 g of Ca(OH)$_2$ was dispersed in 500 mL distilled water. To this solution, Solution C was added gradually under constant and vigorous stirring. After complete addition of Solution C to the Ca(OH)$_2$ dispersion, the stirring was further continued for 6 h. The pH of the solution was about 10. The dispersion was decanted and further dried on a glass tray and warmed at about 50° C. The FTIR (ATR) spectrum of stabilized calcium phosphate IA made using Example 2 is shown in FIG. 4. The FTIR shows the characteristic absorption peaks corresponding to calcium phosphate at 1200-1000 cm$^{-1}$ and 603 cm$^{-1}$. The lack of peaks corresponding to ester peaks (—C=O) at 1730 cm$^{-1}$ and corresponding to vinyl peaks (C=C) at 1642 cm$^{-1}$ indicate the hydrolysis of the ester groups. The spectrum shows characteristic alkyl (C—H—) and alkyloxy (C—O—) peaks, indicating the presence of organic functional groups and the XRD pattern, shown in FIG. 5, is consistent with the characteristic pattern of poorly crystallized hydroxyapatite. As shown in FIG. 6, the EDS of the hydroxy apatite showed that the phosphate group of the Bis 2 had taken part in the reaction, which indicates that the hydroxyapatite was stabilized by the presence of the organic moiety derived from the Bis 2 molecule. The presence of —OH stretching at 3400 cm-1 and 1550 cm-1 was also observed in the FTIR spectrum.

Example 3—Preparation of Stabilized Calcium Phosphate IB—20%

The preparation of stabilized calcium phosphate was done using calcium hydroxide, Bis2 and phosphoric acid. In this case, 24 g. of calcium hydroxide powder was dispersed in 300 mL deionized water and was stirred vigorously. To this solution, a mixture of phosphoric acid (188 g) and 80 g Bis 2 in 300 mL distilled water was added slowly. The calcium hydroxide reacted with phosphoric acid and Bis 2 and formed a clear solution. The pH of the solution was about 3. The stirring was further continued for another 30 min. The solution was labeled as Solution C.

In a 2 L beaker, 78 g of Ca(OH)$_2$ was dispersed in 600 mL distilled water. To this solution, Solution C was added gradually under constant and vigorous stirring. After complete addition of Solution C to the Ca(OH)$_2$ dispersion, the stirring was further continued for 6 h. The pH of the solution was about 10. The dispersion was decanted and further dried on a glass tray and warmed at about 50° C. The FTIR spectrum showed characteristic calcium phosphate, alkyl and alkyloxy peaks and is similar to the spectrum of 1A in example 2.

Example 4—Preparation of Stabilized Calcium Phosphate IC—100%

The preparation of stabilized calcium phosphate was done using calcium hydroxide and Bis 2. In this case, 12 g. of calcium hydroxide powder was dispersed in 300 mL deionized water and was stirred vigorously. To this solution, 120 g Bis 2 dissolved in 100 mL distilled water was added slowly. The calcium hydroxide reacted with Bis 2 exothermally and formed a clear viscous solution. The pH of the solution was about 3.5. The stirring was further continued for another 30 min. The solution was labeled as Solution C.

In a 2 L beaker, 39 g of Ca(OH)$_2$ was dispersed in 300 mL distilled water. To this solution, Solution C was added gradually under constant and vigorous stirring. After complete addition of Solution C to the Ca(OH)$_2$ dispersion, the stirring was further continued for 6 h. The pH of the solution was about 9-10. The dispersion was decanted and further dried on a glass tray and warmed at about 50° C. The material was sticky and could not be pulverized.

Example 5—Preparation of Stabilized Calcium Phosphate II—50%

Figure 7:
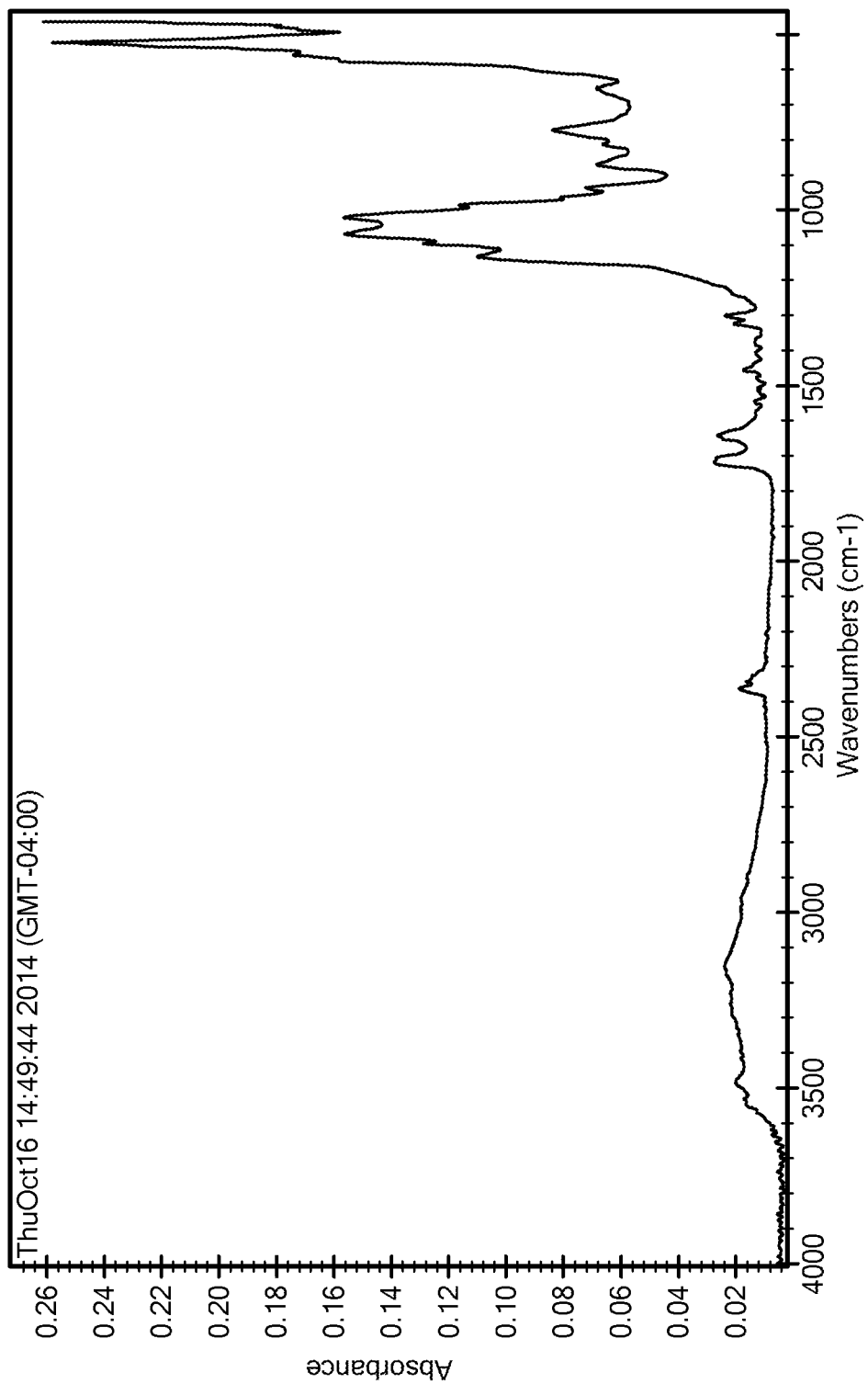
FIG. 7 is a graph showing an FTIR (ATR) spectrum of stabilized calcium phosphate—II made from $CaCl_2$/phosphoric acid and Bis 2 formed according to embodiments of the present invention.
Figure 8:
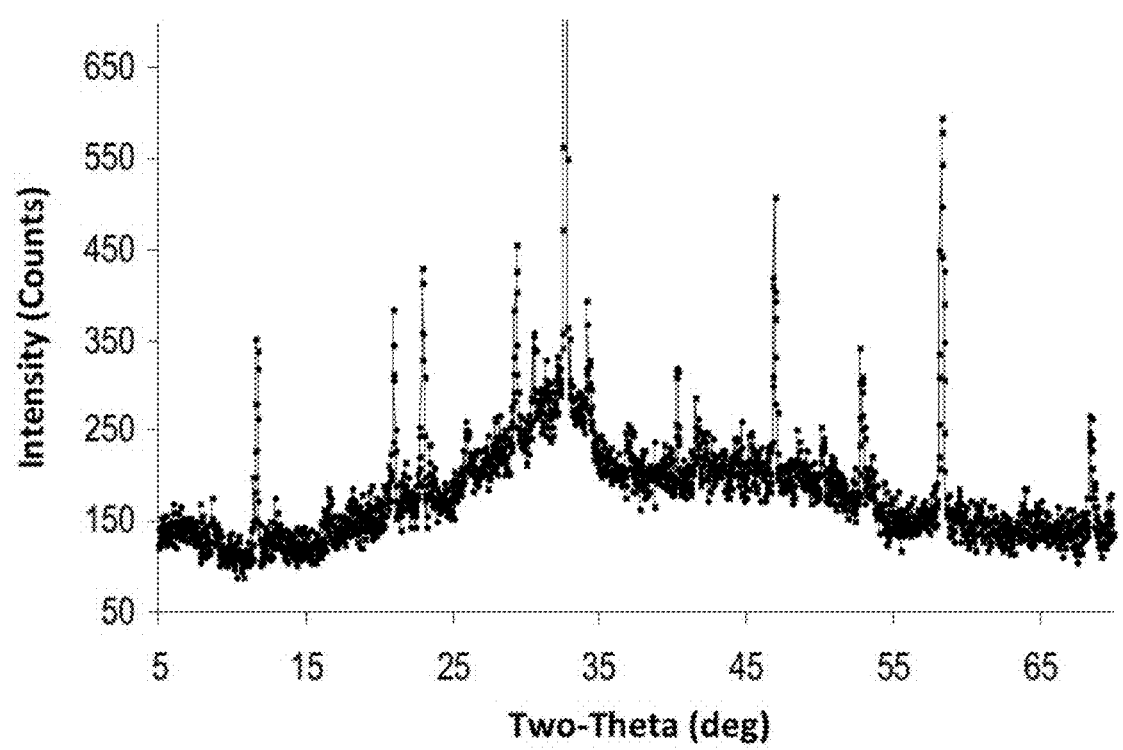
FIG. 8 is a graph showing an XRD pattern of stabilized calcium phosphate—II made from $CaCl_2$/phosphoric acid and Bis 2 formed according to embodiments of the present invention.

The preparation of stabilized calcium phosphate was done using calcium chloride, Bis 2 and phosphoric acid. In a 500 mL 3 neck round bottom flask equipped with thermometer, mechanical stirrer and pH meter, 80 g of calcium chloride dehydrate (0.5517M) was dissolved in 100 mL distilled water. This solution was placed in a water bath at a temperature of about 45° C. To this solution, 50.2 g Bis 2 (0.165M) and 19.22 g H$_3$PO$_4$ (0.165M) dissolved in 50 mL distilled water was added gradually under constant mechanical stirring. After the addition, the mixture was stirred further for another 30 min. To this mixture, ammonium solution was added until calcium phosphate was precipitated and the pH of the solution maintained at pH 10. The suspension was stirred for an additional 12 h at about 45° C. The resulting product was filtered on Whatman filter paper, washed with excess water, until the product was free of ammonia, and dried at about 45° C. for 4 days. The FTIR (ATR) spectrum of stabilized calcium phosphate II made using Example 5 is shown in FIG. 7. The FTIR spectrum shows peaks corresponding to an ester (C=O—) peak at 1730 cm$^{-1}$ and corresponding to a vinyl (C=C) peak at 1642 cm$^{-1}$ in addition to peaks characteristic to calcium phosphate, alkyl groups and alkyloxy groups. The synthesis of hydroxyapatite resulted in hydroxyapatite or calcium phosphate stabilized in a methacrylated phosphate source. The EDS spectrum also showed the presence of Bis 2 group as noted by the carbon content of the calcium phosphate. The synthesis was carried out at lower pH and was always kept below a pH of 10. The calcium phosphate and hydroxyapatite formed have pendent polymerizable methacrylate groups and have polymerizable characteristics. The XRD pattern of stabilized calcium phosphate II made using Example 5 is shown in FIG. 8 and is discussed in more detail below.

Example 6—Preparation of Stabilized Calcium Phosphate III—50%

Figure 9:
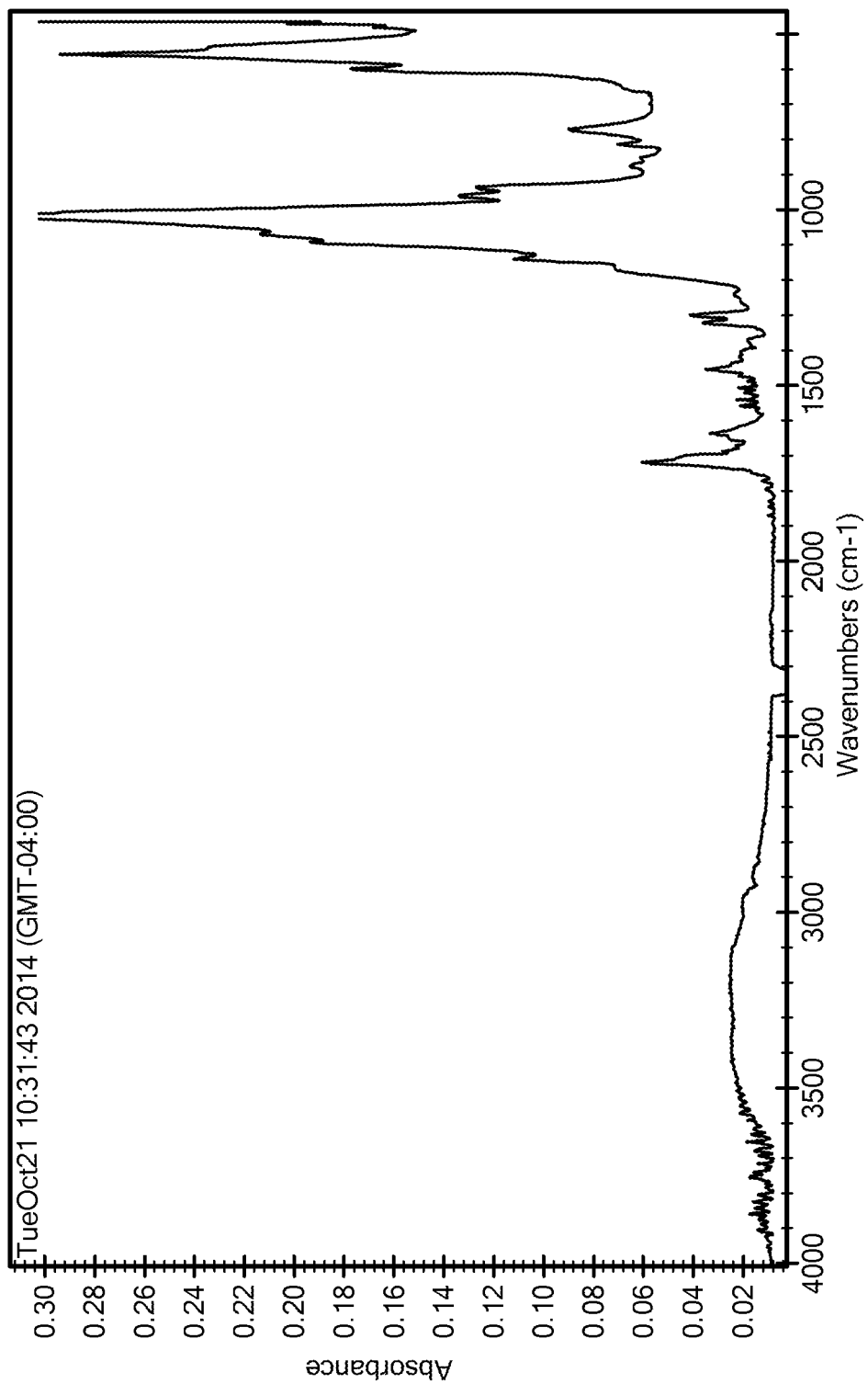
FIG. 9 is a graph showing an FTIR (ATR) spectrum of stabilized calcium phosphate—III made from $CaCl_2$, $Ca(OH)_2$/phosphoric acid and Bis 2 formed according to embodiments of the present invention.
Figure 10:
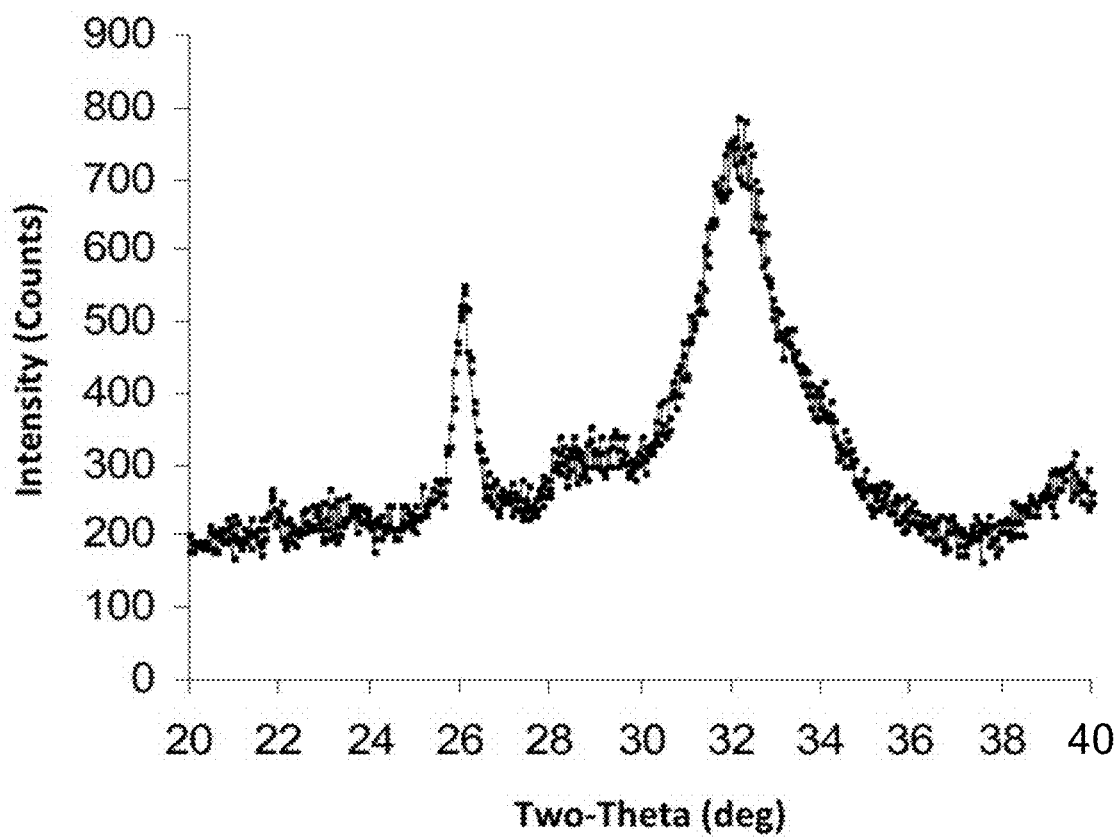
FIG. 10 is a graph showing an XRD pattern of stabilized calcium phosphate—III made from $CaCl_2$, $Ca(OH)_2$/phosphoric acid and Bis 2 formed according to embodiments of the present invention.
Figure 11:
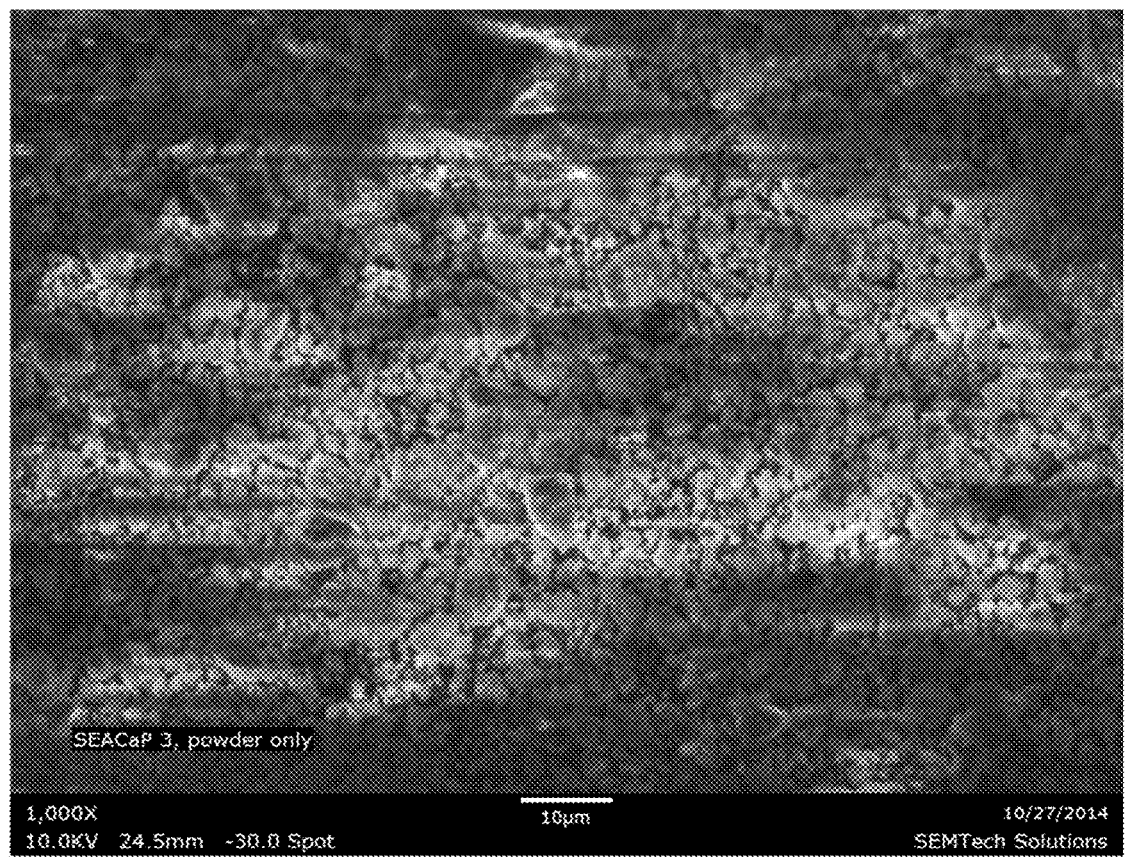
FIG. 11 is a scanning electron micrograph of stabilized calcium phosphate—III made from $CaCl_2$, $Ca(OH)_2$/phosphoric acid and Bis 2 formed according to embodiments of the present invention.

The preparation of stabilized calcium phosphate was done using calcium chloride, calcium hydroxide, Bis 2 and phosphoric acid (made with 70:30 calcium chloride and calcium hydroxide). In a 500 mL 3 neck round bottom flask equipped with thermometer, mechanical stirrer and pH meter, 46.3 g of calcium chloride dehydrate (0.315M) and 10 g calcium hydroxide (0.135M) were dissolved in 60 mL distilled water and placed in a water bath at a temperature of about 45° C. The pH of the solution was about 5. To this solution, 41.31 g Bis 2 (0.135M) and 15.6 g H$_3$PO$_4$ (0.135) dissolved in 50 mL distilled water was added gradually under constant mechanical stirring. After the addition, the mixture was stirred further for another 30 min. To this mixture, ammonia solution was added until calcium phosphate was precipitated and the pH of the solution was maintained at pH 10. The suspension was stirred for an additional 6 h at 45° C. The resulting product was filtered on Whatman filter paper, washed with excess water until the product was free of ammonia and dried at about 45° C. for 4 days. The FTIR (ATR) spectrum of stabilized calcium phosphate III made using Example 6 is shown in FIG. 9. The FTIR spectrum of the material shows peaks corresponding to an ester (C=O—) peak at 1730 cm-1 and corresponding to a vinyl (C=C) peak at 1642 cm-1 in addition to peaks of calcium phosphate (—CaPO), alkyl (C—H) and alkyloxy (C—O) groups. This indicates that the calcium phosphate is stabilized by Bis 2. As shown in FIG. 10, the XRD pattern of the material shows a pattern corresponding to high lattice disorder. The material also exhibits much higher solubility than the control. As shown in FIG. 11, the SEM shows calcium phosphate particles of irregular shapes and low crystallite sizes (mostly less than 10 μm).

Example 7—Preparation of Stabilized Calcium Phosphate IV—100%

Figure 12:
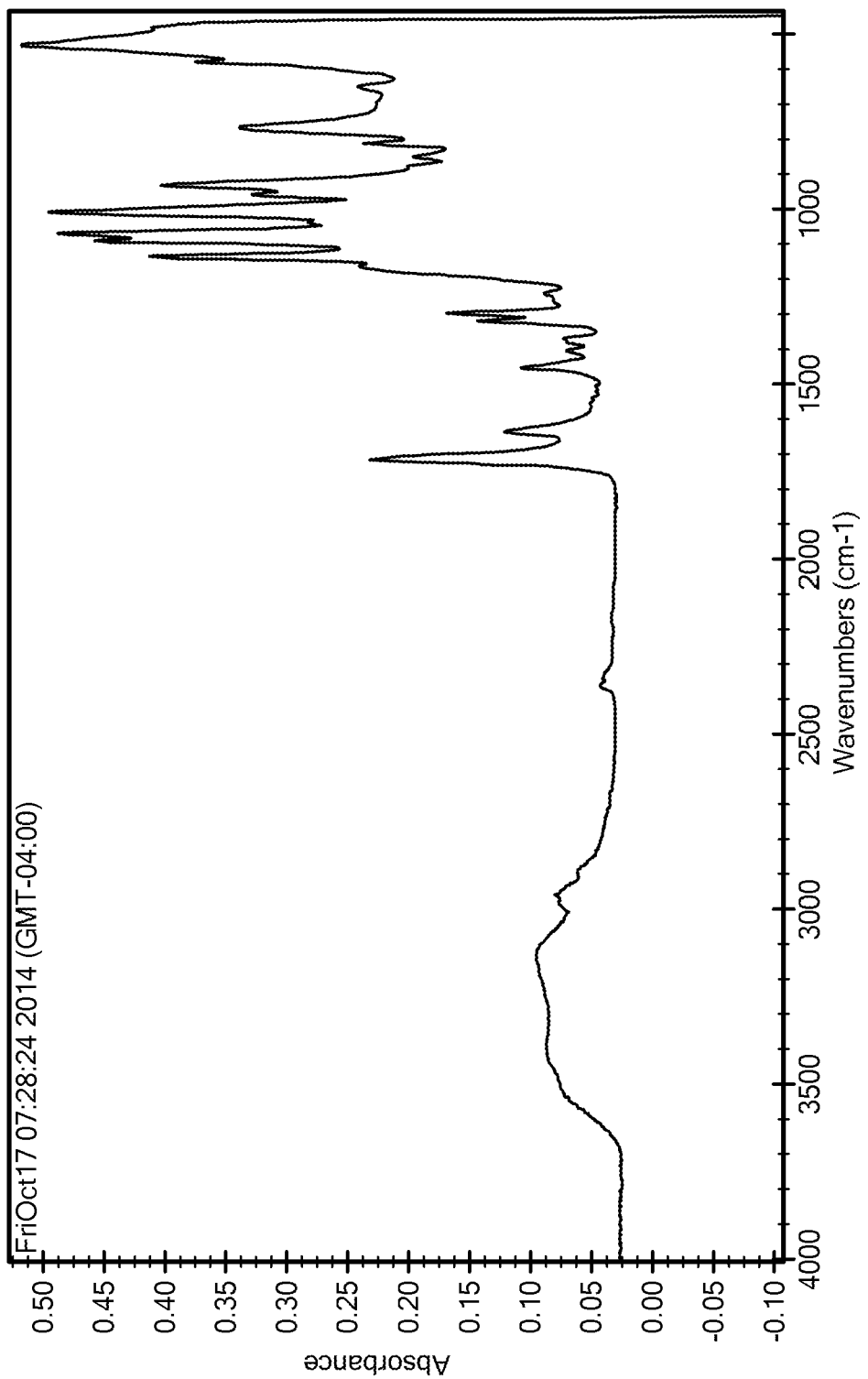
FIG. 12 is a graph showing an FTIR (ATR) spectrum of stabilized calcium phosphate—IV made from $CaCl_2$/100% Bis 2 formed according to embodiments of the present invention.
Figure 13:
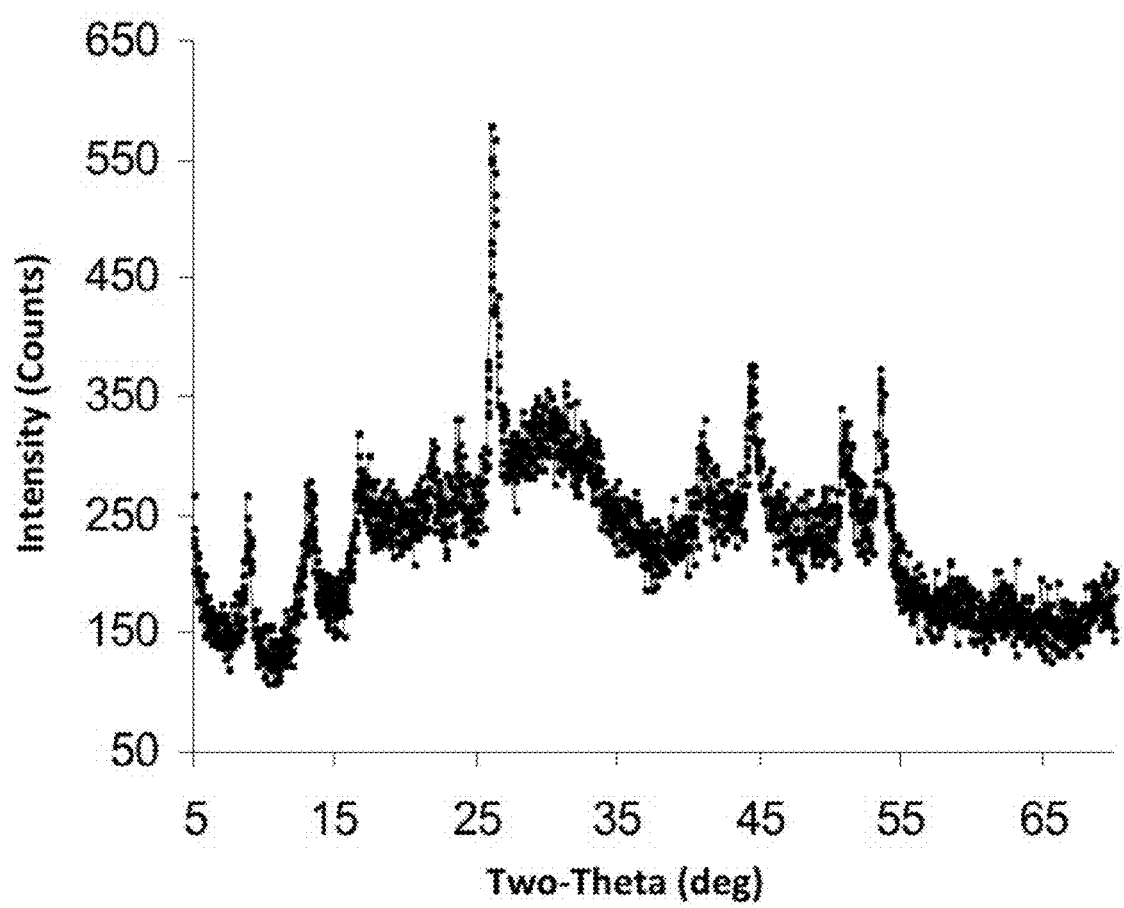
FIG. 13 is a graph showing an XRD pattern of stabilized calcium phosphate—IV made from $CaCl_2$/100% Bis 2 formed according to embodiments of the present invention.
Figure 14:
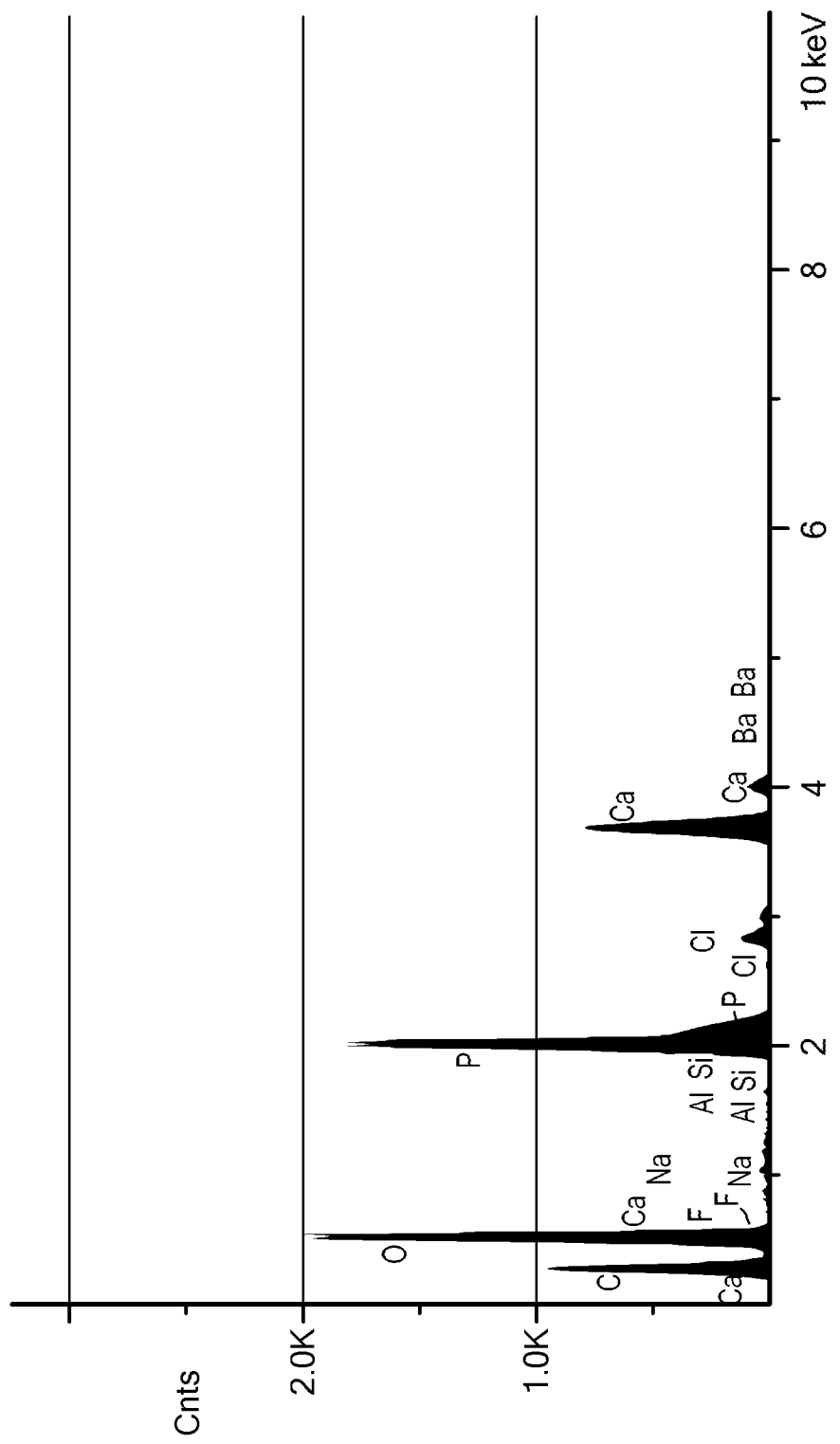
FIG. 14 is a graph showing an EDS analysis of stabilized calcium phosphate—IV made from $CaCl_2$/100% Bis 2 formed according to embodiments of the present invention.

The preparation of stabilized calcium phosphate was done using calcium chloride and Bis 2. In a 500 mL 3 neck round bottom flask equipped with thermometer, mechanical stirrer and pH meter, 74.4 g of calcium chloride dehydrate (0.5M) was dissolved in 100 mL distilled water and placed in a water bath at a temperature of about 45° C. The pH of the solution was about 5. To this solution, 91.8 g Bis 2 (0.5M) dissolved in 50 mL distilled water was added gradually under constant mechanical stirring. After the addition, the mixture was stirred further for another 30 min. To this mixture, ammonium solution was added until calcium phosphate was precipitated and the pH of the solution was maintained at pH 10. The suspension was stirred for an additional 12 h at about 45° C. The resulting product was filtered on Whatman filter paper, washed thoroughly with distilled water until the filtrate was free of ammonia and dried at about 45° C. for 4 days and stored in plastic container. The FTIR (ATR) spectrum of stabilized calcium phosphate IV made using Example 7 is shown in FIG. 12. The FTIR spectrum shows peaks characteristic of calcium phosphate as well as peaks characteristic of methacrylate groups. The material exhibits higher solubility in water and in hydrophilic monomers than the control. As shown in FIG. 13, the XRD pattern corresponds to calcium hydrogen phosphate. As shown in FIG. 14, the EDS analysis shows strong calcium, phosphorous and oxygen peaks. There is also a strong carbon presence, representing the organic functional group.

Example 8—Preparation of Stabilized Calcium Phosphate V—50%

Figure 15:
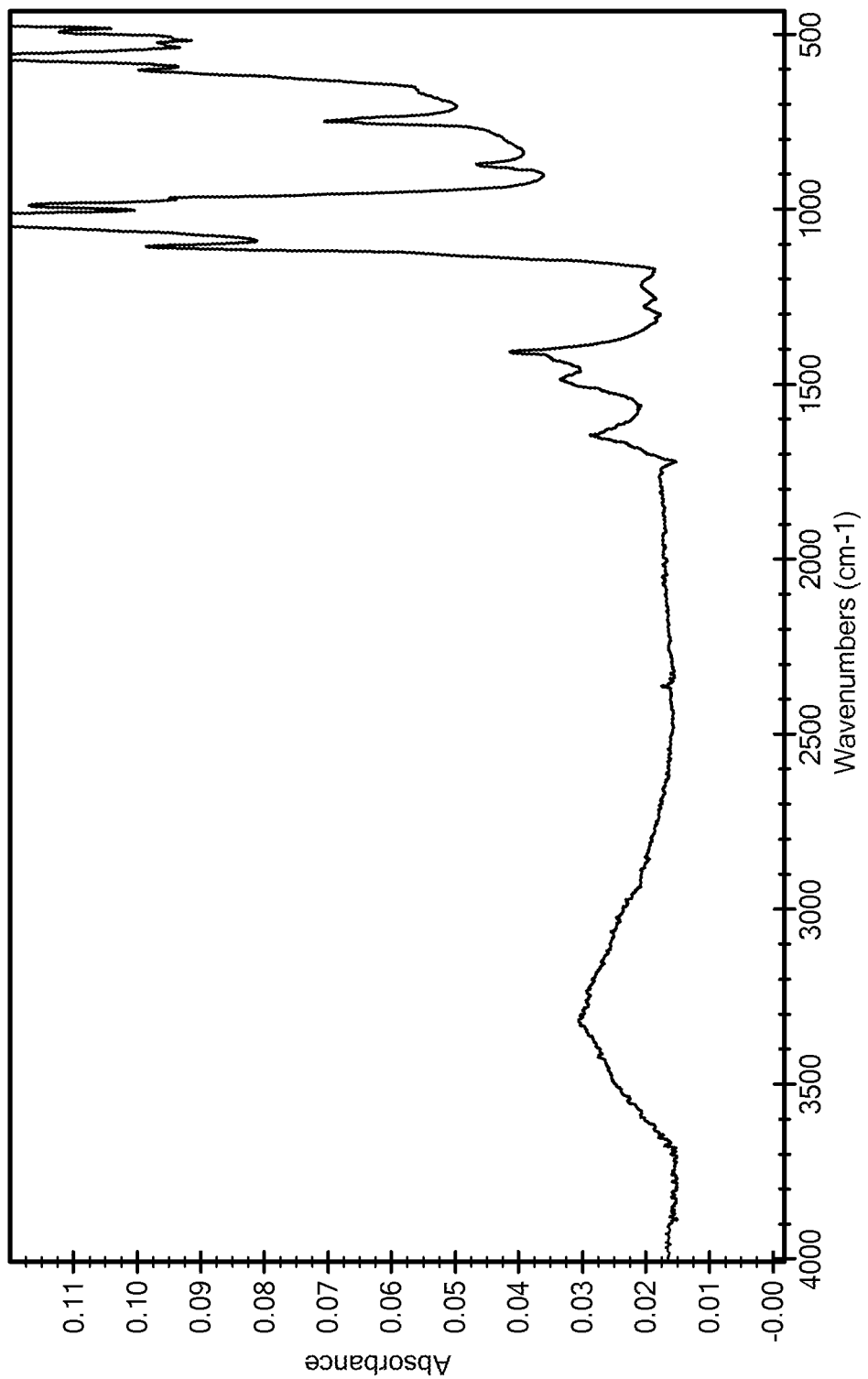
FIG. 15 is a graph showing an FTIR (ATR) spectrum of stabilized calcium phosphate—V made from $Ca(OH)_2$/vinyl phosphonic acid and phosphoric acid formed according to embodiments of the present invention.

The preparation of stabilized calcium phosphate was done using calcium hydroxide, vinyl phosphonic acid and phosphoric acid. 2.4 g calcium hydroxide was dispersed in 30 mL deionized water and stirred vigorously. 4.8 g $H_3PO_4$ and 4.4 g vinyl phosphonic acid were dissolved in 15 mL deionized water. This process is similar to that employed in Example 2. The calcium hydroxide reacted with the $H_3PO_4$-vinyl phosphonic acid mixture and formed a clear solution. The pH of the solution was about 3.5. The stirring was continued for an additional 30 minutes. The solution was labeled as Solution F. Separately, in a 200 mL beaker, 7.8 g of calcium hydroxide was dispersed in 60 mL of deionized water. To this dispersion, Solution F was added gradually under constant and vigorous stirring. After complete addition of Solution F to the calcium hydroxide dispersion, the stirring was further continued for six hours. The pH of the solution was about 10.0. The solution was decanted and the solids dried in a glass tray at 50° C. The FTIR (ATR) spectrum of stabilized calcium phosphate V made using Example 8 is shown in FIG. 15. The FTIR spectrum of the material showed absorption peaks characteristic of calcium phosphate and shows a vinyl (C=C) peak at 1642 $cm^{-1}$. Therefore, the FTIR spectrum shows the material resulted in stabilized hydroxyapatites with end capped vinyl groups which showed the characteristic peak at 1642 $cm^{-1}$. There is no ester group to hydrolyze.

Example 9—Preparation of Polymerizable Dental Resin Composition Using Stabilized Calcium Phosphate IA of Example 2

A 42.0 g resin mix was formed using 65 wt % urethane dimethacrylate, 8 wt % Bis 2, 19 wt % 1,6 hexamethylene dimethacrylate (HMDMA), 4 wt % oligomeric polybutadiene diurethane dimethacrylate and 4 wt % trimethylol propane triacrylate. The resin mixture was then mixed with 0.11 g camphorquinone, 0.2 g 2-dimethylaminoethyl methacrylate) and 0.2 g Ethyl 4-dimethyl amino benzoate as the photoinitiator. This resin mix was then mixed with 30.0 g of stabilized calcium phosphate IA formed according to Example 2, 30.0 g of barium glass and 1.5 g silica to obtain a visible light curable composite. The material showed compressive strength of 302 MPa and flexural strength of 96 MPa. These values are excellent for dental restorative materials. This composite released 510 ug of calcium ion per gram of material at pH 7 and 1030 ug of calcium ion per gram of material at pH 4.

Example 10—Preparation of Polymerizable Dental Resin Composition Using Stabilized Calcium Phosphate IA of Example 2

A 42.0 g resin mix was formed using 65 wt % urethane dimethacrylate, 8 wt % Bis 2, 19 wt % HMDMA, 4 wt % oligomeric polybutadiene diurethane dimethacrylate and 4 wt % trimethylol propane triacrylate. The resin mixture was then mixed with 0.11 g camphorquinone, 0.2 g 2-dimethylaminoethyl methacrylate and 0.2 g Ethyl 4-dimethyl amino benzoate as the photoinitiator. This resin mix was then mixed with 15.0 g of stabilized calcium phosphate IA formed according to Example 2, 45.0 g of barium glass and 1.5 g silica to obtain a visible light curable composite. The material showed compressive strength of 286 MPa and flexural strength of 89 MPa. These values are excellent for dental restorative materials. The material released 232 ug of calcium ion per gram of material at pH 7 and 300 ug of calcium ion per gram of material at pH 4.

Example 11—Preparation of Polymerizable Dental Resin Composition Using Stabilized Calcium Phosphate II of Example 5

A 42.0 g resin mix was formed using 65 wt % urethane dimethacrylate, 8 wt % Bis 2, 19 wt % HMDMA, 4 wt % oligomeric polybutadiene diurethane dimethacrylate and 4 wt % trimethylol propane triacrylate. The resin mixture was then mixed with 0.11 g camphorquinone, 0.2 g dimethylaminoethyl methacrylate and 0.2 g Ethyl 4-dimethyl amino benzoate as the photoinitiator. This resin mix was then mixed with 15.0 g of stabilized calcium phosphate II formed according to Example 5, 45.0 g of barium glass and 1.5 g silica to obtain a visible light curable composite. The material shows compressive strength of 232 MPa and flexural strength of 77 MPa. These values are acceptable for dental restorative materials.

Example 12—Preparation of Polymerizable Dental Resin Composition Using Stabilized Calcium Phosphate III of Example 6

A 42.0 g resin mix was formed using 65 wt % urethane dimethacrylate, 8 wt % Bis 2, 19 wt % HMDMA, 4 wt % oligomeric polybutadiene diurethane dimethacrylate and 4 wt % trimethylol propane triacrylate. The resin mixture was then mixed with 0.11 g camphorquinone, 0.2 g 2-dimethylaminoethyl methacrylate and 0.2 g Ethyl 4-dimethyl amino benzoate as the photoinitiator. This resin mix was then mixed with 15.0 g of stabilized calcium phosphate III formed according to Example 6, 45.0 g of barium glass and 1.5 g silica to obtain a visible light curable composite. The material shows compressive strength of 292 MPa and flexural strength of 109 MPa. These values are excellent for dental restorative materials.

Example 13—Preparation of Polymerizable Dental Resin Composition Using Stabilized Calcium Phosphate III of Example 6

A 42.0 g resin mix was formed using 65 wt % urethane dimethacrylate, 8 wt % Bis 2, 19 wt % HMDMA, 4 wt % oligomeric polybutadiene diurethane dimethacrylate and 4 wt % trimethylol propane triacrylate. The resin mixture was then mixed with 0.11 g camphorquinone, 0.2 g 2-dimethylaminoethyl methacrylate and 0.2 g Ethyl 4-dimethyl amino benzoate as the photoinitiator. This resin mix was then mixed with 75.0 g of stabilized calcium phosphate III formed according to Example 6, 52.5 g of barium glass and 1.5 g silica to obtain a visible light curable composite. The material shows compressive strength of 276 MPa, flexural strength of 123 MPa and diametrical tensile strength of 42 MPa. These values are excellent for dental restorative materials.

To investigate the polymerizing/crosslinking ability of the methacrylate functional calcium phosphate material, visible light polymerization was attempted with a di-functional monomer (1-6 hexamethylene dimethacrylate—HMDMA) and with a mono-functional monomer (2-hydroxyethyl methacrylate—HEMA) using camphorquinone as the photoinitiator and ethyl 4-dimethylamino benzoate as the activator. The material in Example 2 above did not yield a polymer with HEMA; the materials in Examples 6 and 7 yielded polymer composites with adequate compressive strengths (greater than about 90 MPa). A composite made from 50 weight percent HEMA combined with 50 weight percent of the material in Example 6 resulted in an easy-yielding material with a compressive strength of 101 MPa. A composite made from 50 weight percent HEMA combined with 50 weight percent of the material in Example 7 resulted in an easy-yielding material with a compressive strength of 110 MPa. However, a composite made from 50 weight percent HMDMA combined with 50 weight percent of the material in Example 6 resulted in a brittle material with a compressive strength of 151 MPa. A composite made from 50 weight percent HMDMA combined with 50 weight percent of the material in Example 7 resulted in a brittle material with a compressive strength of 125 MPa.

The stability of the calcium phosphate moieties from Examples 2 and 6 were investigated by placing the materials in an incubator at 37° C. for more than 365 days and 140 days, respectively. The materials showed structural as well as chemical integrity. The materials were also found to be stable in acidic monomers for the same periods of time.

In contrast to Example 2, Example 6 is a modified process in which the pH of the reaction mixture is controlled. Specifically, the addition of Bis 2 is carried out at pH 5 and the pH is later adjusted with an ammonia solution to pH 10. This modified process ensures that the ester group is not disrupted by high pH.

The XRD patterns of the materials formed in Examples 2, 5, 6 and 7 are broad and are with low intensities. These are characteristic of high lattice disorders and indicative of very small crystallite sizes. Large number of lattice defects is observed in these materials due to presence of the large Bis 2 molecule. It is known that presence of organic molecules act as impurities and result in low crystalline hydroxypatites. The XRD pattern of the samples formed according to Examples 5 and 7 show that the products are a mixture of calcium salts. The XRD pattern shows the presence of Brushite phases and dicalcium phosphate molecules along with less formed hydroxyapatite. The inventive materials by this formulation do not have to be pure hydroxyapatites, but can also contain substantial amounts of other forms of calcium phosphates as long as the final material provides good resorption of beneficial ions and is able to induce the growth of hydroxyapatites in physiological conditions.

Although the above discussion discloses various exemplary embodiments of the invention, it should be apparent that those skilled in the art may make various modifications that will achieve some of the advantages of the invention without departing from the true scope of the invention.

What is claimed is:

1. A polymerizable composite system for use in dental or biomedical applications, the system comprising:
    stabilized calcium phosphate formed by providing a solution or dispersion including a calcium salt dissolved or dispersed in water or a suitable solvent and reacting bis[2-(methacryloyloxy)ethyl] phosphate with the solution or dispersion in order to form a calcium phosphate moiety having at least one pendant polymerizable group and at least one organic functional group, wherein the solution or dispersion including the calcium salt further includes one or more inorganic phosphate sources selected from the group consisting of phosphoric acid, ammonium phosphate, and pyrophosphoric acid; and
    one or more monomers selected from the group consisting of acidic monomers, hydrophilic monomers, hydrophobic monomers, and combinations thereof.

2. The polymerizable composite system of claim 1, wherein the one or more monomers includes urethane dimethacrylate, bis[2-(methacryloyloxy)ethyl] phosphate, 1,6 hexamethylene dimethacrylate, trimethylol propane triacrylate, hydroxyethyl methacrylate, polyethylene glycol methacrylate, triethylene glycol dimethacrylate, polyethylene glycol dimethacrylate, polylactic acid methacrylate, polycaprolactone methacrylate, bisphenol A glycidyl methacrylate, bisphenol A glycidyl diacrylate, bisphenol A ethoxylate dimethacrylate, bisphenol A dimethacrylate, bisphenol A diglycidyl ether or a combination thereof.

3. The polymerizable composite system of claim 1, further comprising one or more polymers, oligomers, or a combination thereof.

4. The polymerizable composite system of claim 3, wherein the one or more polymers and/or oligomers includes oligomeric polybutadiene diurethane dimethacrylate.

5. The polymerizable composite system of claim 1, further comprising a photoinitiator system.

6. The polymerizable composite system of claim 5, wherein the photoinitiator system includes camphorquinone and an amine or a triphosphene oxide.

7. The polymerizable composite system of claim 1, further comprising a non-reactive filler.

8. The polymerizable composite system of claim 7, wherein the non-reactive filler includes silica, barium glass, strontium glass, quartz, barium sulfate or combinations thereof.

9. The polymerizable composite system of claim 1, further comprising a self-curing system having a reducing agent and an oxidizing agent.

10. The polymerizable composite system of claim 1, further comprising a dual cure system.

11. The polymerizable composite system of claim 1, wherein the one or more inorganic phosphate sources includes phosphoric acid.

* * * * *